US008063102B2

(12) United States Patent
Stock et al.

(10) Patent No.: US 8,063,102 B2
(45) Date of Patent: Nov. 22, 2011

(54) TETRAHYDRONAPHTHALEN-2-OL DERIVATIVES

(75) Inventors: Herman Thijs Stock, Oss (NL); Neeltje Miranda Teerhuis, Oss (NL); Gerrit Herman Veeneman, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 12/721,842

(22) Filed: Mar. 11, 2010

(65) Prior Publication Data

US 2010/0240748 A1    Sep. 23, 2010

Related U.S. Application Data

(60) Provisional application No. 61/159,957, filed on Mar. 13, 2009.

(51) Int. Cl.
*A61K 31/277* (2006.01)
*A61K 31/085* (2006.01)
*A61K 31/05* (2006.01)
*C07C 255/50* (2006.01)
*C07C 43/21* (2006.01)
*C07C 39/17* (2006.01)

(52) U.S. Cl. ........ 514/520; 514/719; 514/729; 558/423; 568/633; 568/719

(58) Field of Classification Search .................. 514/520, 514/719, 548, 729; 568/633, 719; 558/423; 560/139
See application file for complete search history.

(56) References Cited

U.S. PATENT DOCUMENTS 7,531,571 B2    5/2009    Veeneman et al.
7,846,966 B2    12/2010   Veeneman et al.

FOREIGN PATENT DOCUMENTS

| EP | 00200713.6 | 3/2000 |
| WO | WO01/64665 A1 | 9/2001 |
| WO | WO03/044006 A1 | 5/2003 |
| WO | WO2006/088716 A1 | 8/2006 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Chan, K, et al., "Estrogen Receptor Subtypes in Ovarian Cancer," Obstetrics & Gynecology, Jan. 2008, vol. 111, No. 1, pp. 144-151.
Cheng, J., et al., "Expression of estrogen receptor β in prostate carcinoma cells inhibits invasion and proliferation and triggers apoptosis," FEBS Letters, 2004, vol. 566, pp. 169-172.
Cho, M. A., et al., "Expression and role of estrogen receptor α and β in medullary thyroid carcinoma: different roles in cancer growth and apoptosis," Journal of Endocrinology, 2007, vol. 195, pp. 255-263.
Coleman, I. M., et al., "Inhibition of androgen-independent prostate cancer by estrogenic compounds is associated with increased expression of immune-related genes", Neoplasia, 2006, vol. 8, No. 10, pp. 862-878.
Ellem, S. J., et al., "Treating prostate cancer: A rationale for targeting local oestrogens," Nature Reviews Cancer, 2007, vol. 7, No. 8, pp. 621-627.
Grady, D., et al., "MF101, a selective estrogen receptor β modulator for the treatment of menopausal hot flushes: a phase II clinical trial," Menopause, 2009, vol. 16, No. 3, pp. 458-465.
Harris, H.A., et al., "Evaluation of an Estrogen Receptor-β Agonist in Animal Models of Human Disease," Endocrinology, 2003, vol. 144, No. 10, pp. 4241-4249.
Harris, H. A., et al., "A selective estrogen receptor-β agonist causes lesion regression in an experimentally induced model of endometriosis," Human Reproduction, 2005, vol. 20, No. 4, pp. 936-941.
Harris, H. A., "Estrogen Receptor-β: Recent Lessons from in Vivo Studies," Molecular Endocrinology, 2007, vol. 21, No. 1, pp. 1-13.
Hartman, J., et al., "Estrogen Receptor β Inhibits Angiogenesis and Growth of T47D Breast Cancer Xenografts," Cancer Research, Dec. 2006, vol. 66, No. 23, pp. 11207-11213.
Imamov, O., et al. "Estrogen receptor β regulates epithelial cellular differentiation in the mouse ventral prostate," PNAS, 2004, vol. 101, No. 25, pp. 9375-9380.
Lazennec, G., "Estrogen receptor beta, a possible tumor suppressor involved in ovarian carcinogenesis," Cancer Letters, 2006, vol. 231, pp. 151-157.
Leav, I., et al., "Comparative Studies of the Estrogen Receptors β and α and the Androgen Receptor in Normal Human Prostate Glands, Dysplasia, and in Primary and Metastic Carcinoma," American Journal of Pathology, 2001, vol. 159, No. 1, pp. 79-92.
Opas, E. E., et al., "Estrogenic control of thermoregulation in ERαKO and ERβKO mice," Maturitas, 2006, vol. 53, pp. 210-216.
Risbridger, G. P., et al., "Estrogen action on the prostate gland: a critical mix of endocrine and paracrine signaling," Journal of Molecular Endocrinology, 2007, vol. 39, pp. 183-188.
Stella, V. J., et al., "Prodrug strategies to overcome poor water solubility," Advanced Drug Delivery Reviews, 2007, vol. 59, pp. 677-694.
Ullrich, J. W., et al., "Estrogen receptor modulator review," Expert Opinion on Therapeutic Patents, 2006, vol. 16, No. 5, pp. 559-572.
Wada-Hiraike, O., et al., "New developments in oestrogen signalling in colonic epithelium", Biochemistry Society Transactions, 2006, vol. 34, Part 6, pp. 1114-1116.
Walf, A. A., et al., "Antidepressant effects of ERβ-selective estrogen receptor modulators in the forced swim test," Pharmacology, Biochemistry and Behavior, 2004, vol. 78, pp. 523-529.
Walf, A. A., et al., "Erβ-Selective Estrogen Receptor Modulators Produce Antianxiety Behavior and Administered Systemically to Ovariectomized Rats," Neuropsychopharmacology, 2005, vol. 30, pp. 1598-1609.
Written Opinion issued by the International Searching Authority in connection with PCT International Application No. PCT/EP2010/053167, filed Mar. 12, 2010.

* cited by examiner

*Primary Examiner* — Kamal Saeed
*Assistant Examiner* — Kristin Bianchi
(74) *Attorney, Agent, or Firm* — Maria V. Marucci; Valerie J. Camara

(57) ABSTRACT

The present invention relates to novel tetrahydronaphthalen-2-ol derivatives, to pharmaceutical compositions comprising these compounds and to their use in therapy, in particular to their use for the manufacture of a medicament for the prevention or treatment of lower urinary tract symptoms, benign prostate hyperplasia, prostate cancer, hot flushes, anxiety, depression, breast cancer, medullary thyroid carcinoma, ovarian cancer, inflammatory bowel disease, arthritis, endometriosis, and colon cancer.

10 Claims, No Drawings

TETRAHYDRONAPHTHALEN-2-OL DERIVATIVES

The present invention relates to novel tetrahydronaphthalen-2-ol derivatives, to pharmaceutical compositions comprising these compounds and to their use in therapy, in particular to their use for the manufacture of a medicament for the prevention or treatment of lower urinary tract symptoms, benign prostate hyperplasia, and prostate cancer.

The estrogen receptor (ER) is a ligand-activated transcription factor that belongs to the nuclear hormone receptor superfamily. Estrogens play an important role in the regulation of a number of physiological processes, both in females and males. In humans, two different ER subtypes are known: ERα and ERβ, each with a distinct tissue distribution and with different biological roles. ERα has high presence in endometrium, breast cancer cells, ovarian stroma cells and in the hypothalamus. The expression of the ERβ protein has been documented in kidney, brain, bone, heart, lungs, intestinal mucosa, prostate, bladder, ovary, testis and endothelial cells. Subtype-selective ligands may therefore have attractive therapeutic applications in these tissues and organs (for a review see: J. W. Ullrich and C. P. Miller, *Expert Opin. Ther. Patents*, 16 (2006) 559-572).

Benign prostate hyperplasia (BPH), a non-cancerous enlargement of the prostate gland, is a common disorder in elderly men. The condition is characterized by a progressive enlargement of prostatic tissue, resulting in obstruction of the proximal urethra and causing urinary flow disturbances. BPH is associated with both obstructive and irritative voiding symptoms, with bladder outlet obstruction as the most prominent symptom. Obstructive symptoms include straining, hesitancy, decreased force and caliber of the urine stream, an intermittent stream, a sense of incomplete emptying, and terminal dribbling. Irritative symptoms include urinary frequency, urgency, and nocturia. The occurrence of an enlargement of the prostate is thought to be related to many factors, but the presence of androgens in the prostate is a prerequisite. In addition, estrogens also play an important role in proliferation in the prostate. J. Cheng et al. in *FEBS Lett.* 566 (2004) 169-172, suggested that ERβ-selective agonists might be used for the treatment of benign prostatic hyperplasia (BPH) and prostate cancer by inhibiting cell proliferation. Aging βERKO (ERβ knock out) mice develop prostate hyperplasia (O. Imamov et al., *PNAS* 101 (2004) 9375-9380) and upon estradiol treatment these βERKO mice develop prostatic intraepithelial neoplasia (PIN) lesions (precursor of prostate cancer). The αERKO (ERα knock out) mice, on the other hand, do not develop prostate hyperplasia and PIN lesions upon estradiol treatment (G. P. Risbridger et al., *J. Molecular Endocrinology* 39 (2007) 183-188). This finding confirms the protective role of ERβ in the prostate.

The aromatase knock-out (ARKO) mice develop significant prostate hyperplasia. Recently, it was shown that treatment of ARKO mice with an ERβ-selective agonist reduced the hyperplastic lesions in the prostate (see S. J. Ellem and G. P. Risbridger, *Nature Rev. Cancer*, 7 (2007) 621-627). The authors also suggested a possible protective role for ERβ-selective agonists in prostate cancer. Indeed treatment of ARKO mice with estradiol increased PIN lesions, whereas treatment with an ERβ-selective agonist did not result in PIN lesions. The precursor lesion for prostate cancer is high grade PIN, a form of hyperplasia in the peripheral zone of the prostate. Therefore, ERβ-selective agonists might also be used as a treatment for patients with high grade PIN to prevent or delay the onset of prostate cancer. Moreover, another study demonstrated that the presence of ERβ prevented prostate cancer in a preclinical prostate cancer model (I. M. Coleman et al., *Neoplasia* 8 (2006) 862-878). It has also been described that ERβ is expressed in prostate cancer metastasis and especially bone, suggesting a protective role of ERβ in prostate cancer bone metastasis (I. Leav et al., *Am. J. Pathol.* 159 (2001) 79-92).

Prostate cancer is the most common cancer diagnosed in men. Prostate carcinoma originates in the peripheral zone of the prostate. The process of carcinogenesis occurs in epithelial tissue and is initiated following genetic damage to the epithelial cells. Sex steroids play a key role in prostate cancer progression, especially the 17β-estradiol/testosterone (E2/T) ratio.

The process of prostate carcinogenesis occurs with long latency periods. Prostatic intraepithelial neoplasia (PIN), a precursor of prostate cancer, has been observed in young men. Progression of PIN to high grade PIN may take another 10 years. After this, it may take several years for metastatic cancer to develop. High grade PIN predominantly occurs in the peripheral zone of the prostate, where 70% of prostate cancers arise. The long latent period provides important opportunity to prevent the development of invasive metastasis cancer (bone cancer is a common prostate cancer metastasis). However, due to the long latency period some men may never be treated for prostate cancer and eventually die of other causes. Drug therapy aims to inhibit the growth of androgen-dependent tumors and to prevent their progression into hormone-independent metastasis stages. Androgen ablation therapy has been shown to produce the most beneficial effect in patients with hormone-responsive prostate tumors (grade III and metastatic tumors). However, hormone therapy frequently results in hormone refractory prostate tumors after approximately 3-5 years of treatment.

Thus, although there are a number of treatments available for BPH and prostate cancer, there remains a need for alternative compounds and treatments.

The use of ERβ-selective ligands for other therapeutic indications has also been implicated. The specific activity of ERβ in the regulation of hot flushes has been described (E. E. Opas et al., *Maturitas*, 53 (2006) 210-216; D. Grady et al., *Menopause*, 16 (2009) 458-465).

The specific antianxiety behavioral effect of ERβ has been described (A. A. Walf and C. A. Frye, *Neuropsychopharmacology*, 30 (2005) 1598-1609). Moreover, a potential beneficial effect of ERβ on depressive behavior was observed (A. A. Walf et al., *Pharmacol. Biochem. Behav.*, 78 (2004) 523-529).

Introduction of ERβ in the breast cancer cell line T47D, was shown to inhibit tumor growth by inhibiting angiogenesis (J. Hartman et al., *Cancer Res.*, 66 (2006) 11207-11213).

Infection of ER-negative medullary thyroid carcinoma TT cells with ERβ suppressed the growth of these cells. Furthermore, apoptosis was detected in the ERβ-infected cells (M. A. Cho et al., *Journal of Endocrinology*, 195 (2007) 255-263).

A role for ERβ in folliculogenesis has also been described, since ERβ knock out mice displayed fewer corpora lutea than their wild type counterparts (H. A. Harris, *Mol. Endocrinol.*, 21 (2007) 1-13).

In ovarian cancer, a link was made between loss of ERβ expression and malignant transformation. ERβ expression was significantly higher in stage I disease compared with stage II-IV disease. A higher ERβ expression was found to be significantly associated with a longer disease-free survival as well as overall survival (K. K. L. Chan et al., *Obstet. Gynecol.*, 111 (2008) 144-151). Moreover, introduction of ERβ in an ovarian cancer cell line reduced proliferation and invasion and increased cellular apoptosis (G. Lazennec, *Cancer Lett.*, 231 (2006), 151-157).

It has been shown that an ERβ-selective ligand treated chronic intestinal inflammation in HLA-B27 mice and was effective at reducing joint swelling in an adjuvant-induced rheumatoid arthritis model (H. A. Harris et al., *Endocrinology*, 144 (2003) 4241-4249) and therefore has therapeutic potential in inflammatory bowel disease and/or arthritis.

This anti-inflammatory effect of ERβ-selective ligands has also been demonstrated in another model for chronic inflammation. An ERβ-selective compound reduced endometrial lesions in an experimentally induced endometriosis model (H. A. Harris et al., *Hum. Reprod.*, 20 (2005) 936-941).

The protective role of ERβ in colon cancer has been described by O. Wada-Hiraike et al. in *Biochem. Soc. Trans.*, 34 (2006) 1114-1116).

Selective estrogen receptor β (ERβ) compounds are known in the prior art. WO 01/64665 discloses chroman derivatives, which are shown to be selective agonists for ERβ over ERα. These compounds are described to be useful in estrogen receptor-related medical treatments, such as those for contraception or for treatment or prevention of benign prostate hypertrophy, cardiovascular disorders, menopausal complaints, osteoporosis, estrogen dependent tumour control or central nervous system disorders such as depression or Alzheimer's disease. They are particularly suitable for the treatment of osteoporosis, cardiovascular disorders, prostate disorders and central nervous system disorders such as depression or Alzheimer's disease, but no biological activity data on any of these therapeutic indications are provided.

Compounds with a 1-benzyl-3-phenyl-tetralone (or tetrahydronaphthalene) skeleton, analogous to the chroman derivatives disclosed in WO 01/64665, have been mentioned in EP 00200713.6, but no specific examples of such compounds have actually been disclosed therein.

WO 03/044006 discloses substituted benzopyrans as selective estrogen receptor β agonists, which are described to be useful in the treatment of prostate cancer, benign prostatic hyperplasia, testicular cancer, ovarian cancer, lung cancer, cardiovascular diseases, neurodegenerative disorders, urinary incontinence, central nervous system (CNS) disorders, gastrointestinal (GI) tract disorders, and osteoporosis. The selectivity of said benzopyrans for ERβ over ERα is low. No in vivo data are shown.

WO 2006/088716 discloses substituted tetralins as selective estrogen receptor β agonists, which are described to be useful in the treatment of benign prostatic hypertrophy, obesity, dementia, hypertension, incontinence, colon cancer, prostate cancer, infertility, depression, leukemia, inflammatory bowel disease, and arthritis. No data for the selectivity of said tetralins for ERβ over ERα and no in vivo data are shown.

The present invention provides a series of tetrahydronaphthalen-2-ol derivatives, more in particular 6-(4-hydroxyphenyl)-5,6,7,8-tetrahydronaphthalen-2-ol derivatives, which are selective ERβ agonists and which can be used inter alia for the prevention or treatment of LUTS, BPH, and prostate cancer, of the following Formula 1

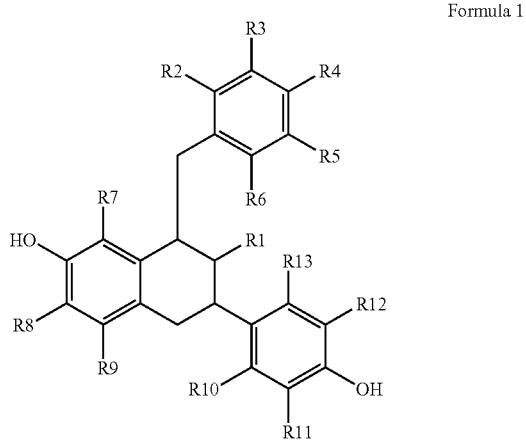

Formula 1 wherein
R1 is (C1-C4)alkyl, (C2-C4)alkenyl or (C2-C4)alkynyl, independently optionally substituted with one or more halogen, R1 having a cis-orientation in relation to both the exocyclic phenyl group at the 6-position and the benzyl group at the 8-position of the skeleton;
R2-R13 are independently H, halogen, CN, OH, (C1-C4) alkyl, optionally substituted with one or more halogen or (C1-C2)alkoxy;
or a prodrug or an isotopically-labelled derivative thereof.

The compounds of this invention contain three centers of chirality and because of the cis-orientation of the substituents at C6, C7 and C8 of the tetrahydro-naphthalen-2-ol skeleton, can exist as a racemic mixture of enantiomers, containing substantially equal amounts of the two enantiomers, as mixtures of enantiomers in any proportions or as the pure enantiomers. The present invention includes the aforementioned mixtures and racemic mixtures within its scope and each of the individual (+) and (−) enantiomers substantially free of the other enantiomer, i.e. an enantiomer associated with less than 5%, preferably less than 2%, in particular less than 1% of the other enantiomer.

The compounds of the present invention show a surprisingly high metabolic stability in human hepatocytes, in particular when compared to corresponding chroman compounds, some of which compounds are disclosed in WO 01/64665. Drugs are most often eliminated from the body by biotransformation and/or excretion into bile or urine. The liver is the major organ for biotransformation of xenobiotics. Biotransformation is achieved via two major enzymatic routes in the liver: structural modification (Phase I metabolism) or conjugation (Phase II metabolism). A reduced rate of metabolism (i.e. higher metabolic stability) will result in higher and more prolonged plasma levels of a drug.

The compounds of the present invention are subtype-selective estrogen receptor β (ERβ) agonists with high selectivity over the estrogen receptor α (ERα). The presence of ERα agonistic activity in a drug will contribute to unwanted ERα-mediated side effects, like feminization. When drugs have reduced ERβ agonistic selectivity over ERα, the ERα-mediated side effects will become apparent at lower doses. Thus, drugs are preferred with highest ERβ agonistic selectivity over ERα.

The skeleton of the compounds in this invention contains three chiral centres, with an all-cis configuration. Such compounds can exist as two different enantiomers, which are 3-dimensional mirror images of each other. In one enantiomer the three chiral centres are all directed upwards relative to the plain of the scaffold and in the other enantiomer they are all directed downwards. The single enantiomer with highest activity on a biological target is defined as the eutomer on that target; the enantiomer with the lowest activity is defined as the distomer on that target. The ratio of the activities of the eutomer and the distomer is called the eudismic ratio. We observed that for the compounds of the present invention, the eutomers on ERβ have relatively low ERα agonistic activity, whereas the distomers on ERβ have relatively high ERα agonistic activity. In other words, for the compounds in accordance with the present invention we found, unexpectedly, that the eudismic ratio on ERβ is (much) higher than on ERα. Thus, unexpectedly, the eutomers have higher ERβ agonistic selectivity over ERα than the distomers.

Thus, in a further embodiment of the present invention a series of tetrahydro-naphthalen-2-ol derivatives of the following Formula 2 is provided, with the indicated absolute stereochemistry

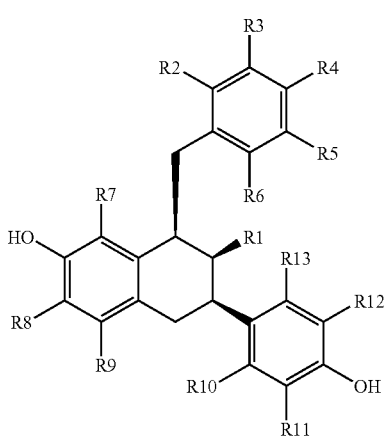

Formula 2 wherein

R1 is (C1-C4)alkyl, (C2-C4)alkenyl or (C2-C4)alkynyl, independently optionally substituted with one or more halogen, R1 having a cis-orientation in relation to both the exocyclic phenyl group at the 6-position and the benzyl group at the 8-position of the skeleton;

R2-R13 are independently H, halogen, CN, OH, (C1-C4) alkyl, optionally substituted with one or more halogen or (C1-C2)alkoxy;

or a prodrug or an isotopically-labelled derivative thereof.

The alkyl, alkenyl and alkynyl group may be linear or branched. Suitable examples include methyl, ethyl, isopropyl, tertiary butyl, ethenyl, propen-2-yl, ethynyl and propynyl. Halogen means fluorine, chorine, bromine and iodine, in particular fluorine and chlorine. A particularly suitable (C1-C4)alkyl group substituted with one or more halogen is a trifluoromethyl group.

In one embodiment of the present invention, R1 is (C1-C4) alkyl, optionally substituted with one or more halogen.

A prodrug is defined as being a compound which is converted in the body of a recipient to a compound as defined by Formula 1. Notably, the hydroxyl groups at the 6-phenyl substituent or at the 2-position of the skeleton of Formula 1 can for example be substituted by an alkyl, alkenyl, acyl, aroyl, alkoxycarbonyl, alkylsulfonyl, arylsulfonyl, alkylsulfamate, arylsulfamate, phosphate group or glycosyl group, whereby the carbon chain length is not considered to be sharply delimited, while aroyl and aryl generally will comprise a phenyl, pyridinyl or pyrimidinyl, which groups can have substitutions customary in the art, such as alkyl, hydroxy, halogen, nitro, cyano, and (mono-, or dialkyl)amino groups. The carbon chain length is selected depending on the desired properties of the prodrugs, whereby the longer chained prodrugs with for example lauryl or caproyl chains generally are more suitable for sustained release and depot preparations. It is known that such substituents spontaneously hydrolyze or are enzymatically hydrolyzed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound. Also the resulting plasma concentration of the parent compound after administration of the prodrug may differ from the resulting plasma concentration after direct administration of the parent compound. For other types of prodrugs it should be realized that the hydroxyl groups in compounds according to Formula 1 can be placed in position by the metabolic system of the recipient. The hydroxyl groups give an important contribution to the affinity for the estrogen receptor. Thus, compounds as defined by Formula 1, but lacking one or both hydroxyl groups are also made available as compounds according to this invention, and which compounds are referred to as prodrugs.

In one embodiment, the hydroxyl group at the 6-phenyl substituent and/or at the 2-position of the skeleton of Formula 1 is substituted with a (C1-C8)alkyl, (C1-C18)acyl, glucosyl or glucuronyl group, in a further embodiment with a (C1-C4) alkyl, (C1-C8)acyl or glucuronyl group. Representative examples of such prodrugs are described in Tables 2 and 4 hereinbelow.

Prodrugs of tetrahydronaphthalen-2-ol derivatives of Formula 1 may be prepared to increase their aqueous solubility in order to facilitate pharmaceutical formulation and/or to improve bioavailability following various routes of administration (e.g. intestinal absorption after oral administration). Such solubilizing prodrugs are well known to those of skill in the art. Representative examples of this approach can be found in V. J. Stella and W. N.-A. Kwame, *Advanced Drug Delivery Reviews*, 59 (2007) 677-694.

The present invention also embraces isotopically-labelled derivatives of any of the compounds according to Formula 1, which are identical to those recited herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulphur, fluorine, chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively. Certain isotopically-labelled derivatives of the compounds of Formula 1 (e.g. those labelled with $^{3}H$ and $^{14}C$) are useful in compound and/or substrate tissue distribution assays. Tritiated (i.e. $^{3}H$) and carbon-14 (i.e. $^{14}C$) isotopes are particularly preferred for their ease of preparation and detectability. Certain isotopically-labelled compounds of Formula 1 can be useful for medical imaging purposes. E.g., those labelled with positron-emitting isotopes like $^{11}C$ or $^{18}F$ can be useful for application in Positron Emission Tomography (PET) and those labelled with gamma ray emitting isotopes like $^{123}I$ can be useful for application in Single Photon Emission Computed Tomography (SPECT). Further, substitution with heavier isotopes such as deuterium (i.e. $^{2}H$) may afford certain therapeutic advantages resulting from greater metabolic stability (e.g. increased in vivo half-life or reduced dosage requirements) and hence may be preferred in some circumstances. Isotopically-labelled compounds of Formula 1, in particular those containing isotopes with longer half lives (T½>1 day), can generally be prepared by following procedures analogous to those disclosed in the Schemes and/or in the Examples hereinbelow, by substituting an appropriate isotopically-labelled reagent for a non-isotopically labelled reagent.

In another embodiment, the present invention provides tetrahydronaphthalen-2-ol derivatives of Formula 1

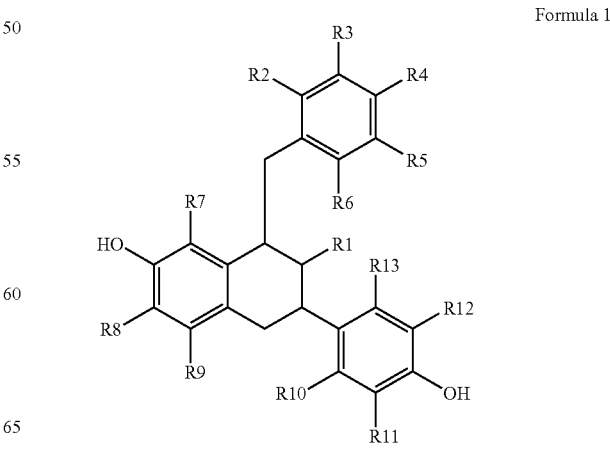

Formula 1 wherein

R1 is (C1-C4)alkyl, (C2-C4)alkenyl or (C2-C4)alkynyl, independently optionally substituted with one or more halogen, $R^1$ having a cis-orientation in relation to both the exocyclic phenyl group at the 6-position and the benzyl group at the 8-position of the skeleton;

R2-R6 are independently H, halogen, CN, OH, (C1-C4)alkyl, optionally substituted with one or more halogen or (C1-C2)alkoxy, with a maximum of two OH groups;

R7-R13 are independently H, halogen, CN, (C1-C4)alkyl, optionally substituted with one or more halogen or (C1-C2)alkoxy;

or a prodrug thereof.

In yet another embodiment, the present invention provides tetrahydronaphthalen-2-ol derivatives of Formula 1

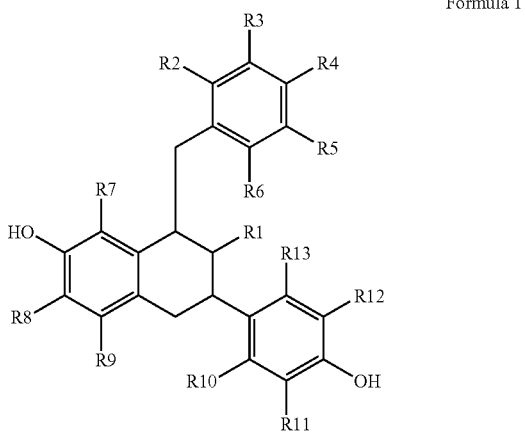

Formula 1 wherein

R1 is (C1-C4)alkyl, (C2-C4)alkenyl or (C2-C4)alkynyl, independently optionally substituted with one or more halogen, $R^1$ having a cis-orientation in relation to both the exocyclic phenyl group at the 6-position and the benzyl group at the 8-position of the skeleton;

R2-R13 are independently H, halogen, CN, OH, (C1-C4) alkyl, optionally substituted with one or more halogen or (C1-C2)alkoxy, with a maximum of five R2-R13 groups unequal to H.

In a further embodiment of the present invention, there are from zero to three R2-R13 groups unequal to H, in particular from one to three R2-R13 groups unequal to H.

In another embodiment, the present invention provides tetrahydronaphthalen-2-ol derivatives of Formula 1

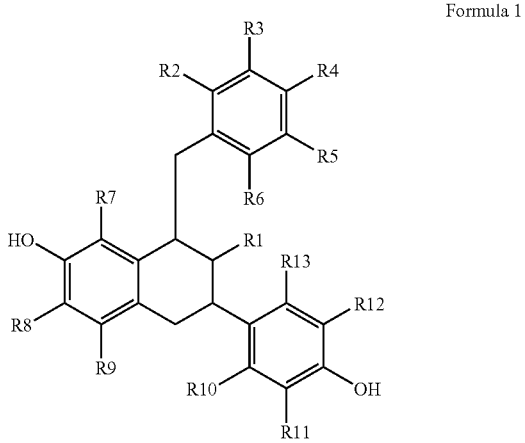

Formula 1 wherein

R1 is methyl, ethyl or propyl;

R2 is H, chlorine, fluorine, CN, methoxy or methyl;

R3-R7 and R10 are H or fluorine;

R8, R9, R11 and R13 are H;

R12 is H, fluorine or methyl.

In a further embodiment of the present invention, the tetrahydronaphthalen-2-ol derivative is selected from the group consisting of compounds according to Formula 1 wherein R1 is methyl, R2 is fluorine, and R3-R13 are H; R1 is ethyl, R2 is fluorine, and R3-R13 are H; R1 is methyl, R2 and R6 are fluorine, and R3-R5 and R7-R13 are H; R1 is methyl, R2 is CN, and R3-R13 are H; R1 is ethyl, R2 and R12 are fluorine, and R3-R11 and R13 are H; and R1 is ethyl, R4 is fluorine, and R2-R3 and R5-R13 are H. In an even further embodiment of the present invention, the tetrahydronaphthalen-2-ol derivative is a compound of Formula 1 wherein R1 is methyl, R2 is fluorine, and R3-R13 are H (i.e. compound 9a).

In a further embodiment, the present invention provides tetrahydronaphthalen-2-ol derivatives of Formula 2, with the indicated absolute stereochemistry

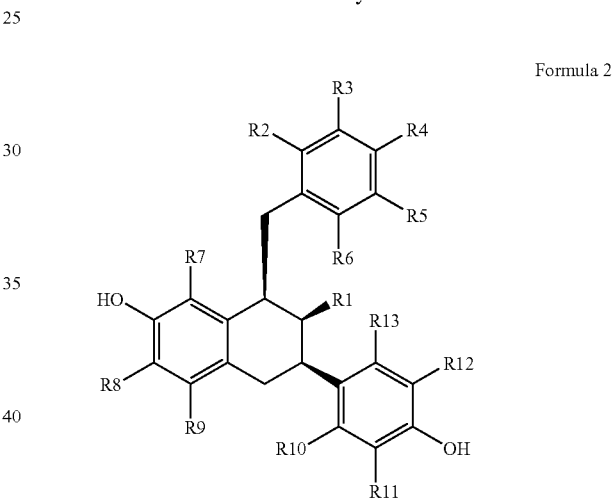

Formula 2 wherein

R1 is methyl, ethyl or propyl;

R2 is H, chlorine, fluorine, CN, methoxy or methyl;

R3-R7 and R10 are H or fluorine;

R8, R9, R11 and R13 are H;

R12 is H, fluorine or methyl.

In a further embodiment of the present invention, the tetrahydronaphthalen-2-ol derivative is selected from the group consisting of compounds according to Formula 2 wherein R1 is methyl, R2 is fluorine, and R3-R13 are H; R1 is ethyl, R2 is fluorine, and R3-R13 are H; R1 is methyl, R2 and R6 are fluorine, and R3-R5 and R7-R13 are H; R1 is methyl, R2 is CN, and R3-R13 are H; R1 is ethyl, R2 and R12 are fluorine, and R3-R11 and R13 are H; and R1 is ethyl, R4 is fluorine, and R2-R3 and R5-R13 are H. In an even further embodiment of the present invention, the tetrahydronaphthalen-2-ol derivative is a compound of Formula 2 wherein R1 is methyl, R2 is fluorine, and R3-R13 are H (i.e. compound 11a).

The compounds of the present invention can be produced by various methods known in the art of organic chemistry. The general synthetic procedures used to prepare the compounds described in the examples below are depicted in the following reaction schemes. Variations to these schemes can easily be made by one skilled in the art. In the following schemes, PG refers to any suitable protecting group and the R groups are as defined in Formula 1 or 2 above, and where needed the R group is capped with a suitable protecting group during the synthesis.

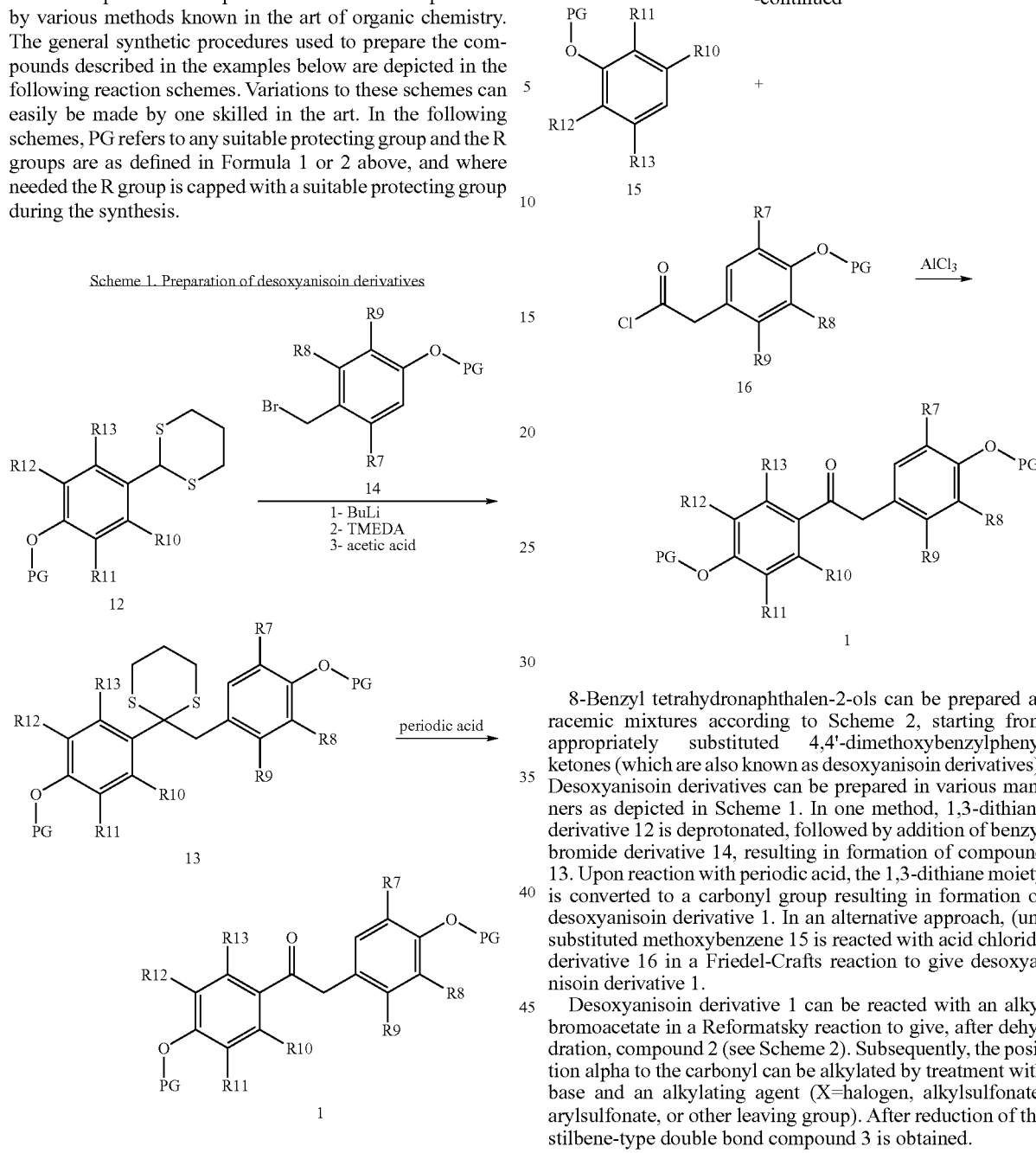

8-Benzyl tetrahydronaphthalen-2-ols can be prepared as racemic mixtures according to Scheme 2, starting from appropriately substituted 4,4'-dimethoxybenzylphenyl ketones (which are also known as desoxyanisoin derivatives). Desoxyanisoin derivatives can be prepared in various manners as depicted in Scheme 1. In one method, 1,3-dithiane derivative 12 is deprotonated, followed by addition of benzyl bromide derivative 14, resulting in formation of compound 13. Upon reaction with periodic acid, the 1,3-dithiane moiety is converted to a carbonyl group resulting in formation of desoxyanisoin derivative 1. In an alternative approach, (un)substituted methoxybenzene 15 is reacted with acid chloride derivative 16 in a Friedel-Crafts reaction to give desoxyanisoin derivative 1.

Desoxyanisoin derivative 1 can be reacted with an alkyl bromoacetate in a Reformatsky reaction to give, after dehydration, compound 2 (see Scheme 2). Subsequently, the position alpha to the carbonyl can be alkylated by treatment with base and an alkylating agent (X=halogen, alkylsulfonate, arylsulfonate, or other leaving group). After reduction of the stilbene-type double bond compound 3 is obtained.

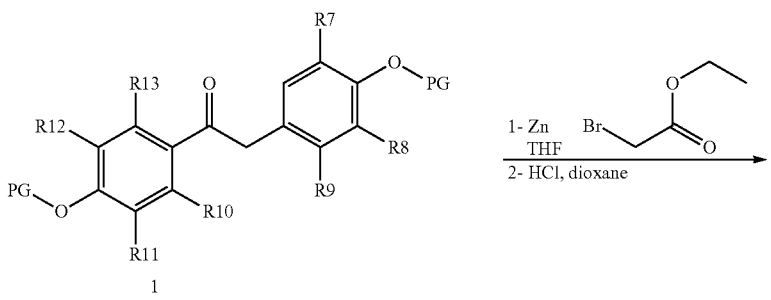

-continued
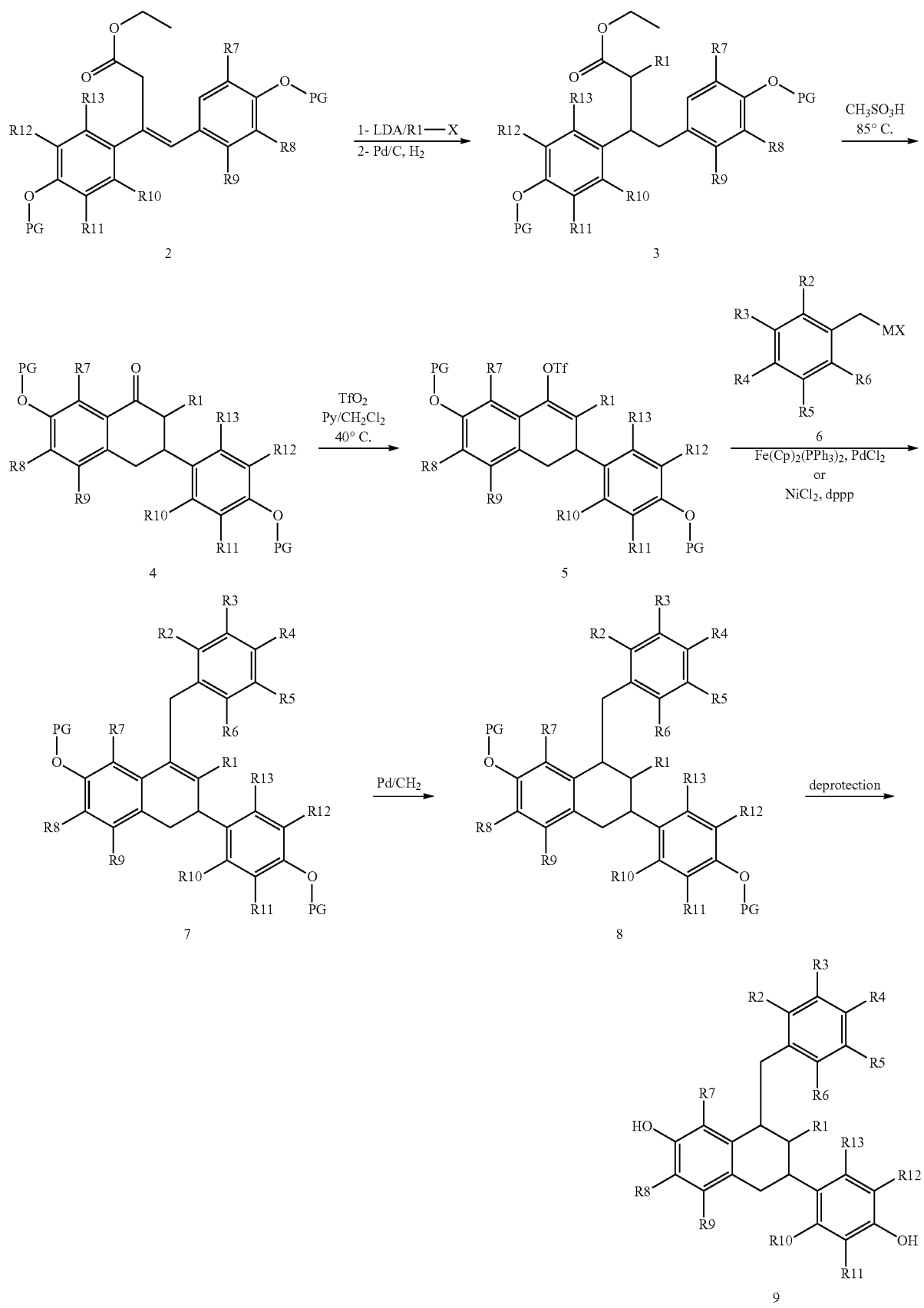

Alternatively, compound 3 can be prepared directly from compound 1 by reaction with an α-bromo,α-alky ester 17 that already contains substituent R1, followed by elimination of water and reduction of the stilbene-type double bond, as depicted in Scheme 3.

removed at an earlier stage in the synthetic sequence. For example, deprotection may be performed at the stage of compound 5. In case PG=methyl, deprotection of compound 5 may be achieved by reaction with boron tribromide to give unprotected bisphenol 20 (see Scheme 4). Compound 20 can

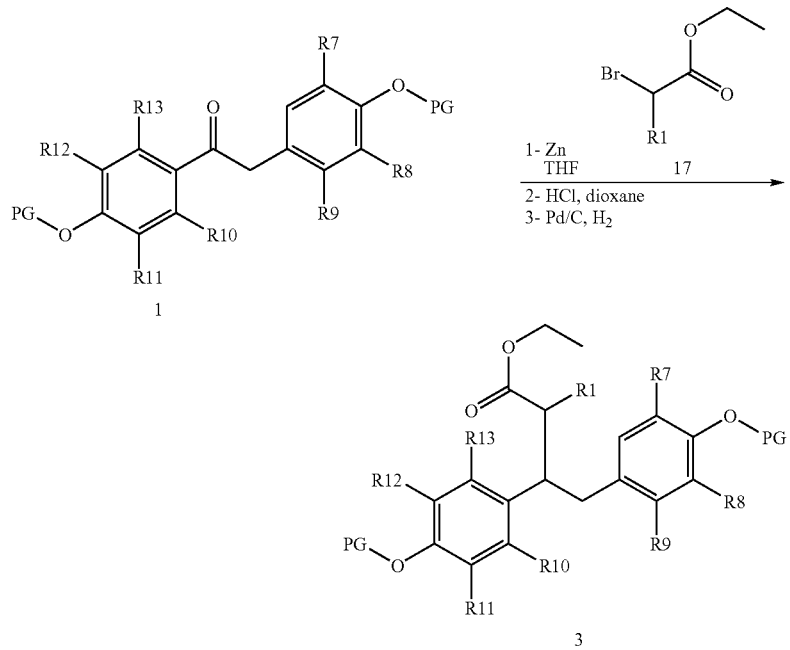

Scheme 3. Alternative preparation of compound 3

Under acidic conditions compound 3 can be cyclized to tetralone 4 (see Scheme 2). Tetralone 4 can be converted to enol triflate 5 by reaction with trifluoromethanesulfonic anhydride. Enol triflate 5 can be converted to compound 7 by a palladium- or nickel-catalyzed coupling reaction with organometallic reagent 6 (M=Zn, Mg; X=halogen). Reduction of the non-aromatic double bond in 7 can be achieved by Pd-catalyzed hydrogenation to give compound 8. The protecting groups in compound 8 can be removed by various methods known in the art of organic chemistry, depending of the nature of the applied protecting groups. For example, when PG=methyl, removal of the protecting groups can be achieved by reaction with boron tribromide to afford the bis-phenolic compound 9, as a racemic mixture of enantiomers.

Compounds 9 in which R1 is (C2-C4)alkenyl or (C2-C4) alkynyl can be prepared from corresponding compounds 9 in which R1 is 2-fluoroethyl, which can be synthesized according to Scheme 2. The fluoroethyl group can subsequently be converted to alkenyl or alkynyl groups by various methods known in the art of organic chemistry, for example by conversion of 2-fluoroethyl to 2-bromoethyl followed by elimination of HBr to give compound 9 in which R1 is ethenyl. Alternatively, the 2-bromoethyl substituent can undergo a substitution reaction with an organometallic reagent to introduce an alkenyl or alkynyl group. Alternatively, alkenyl groups may be converted to alkynyl groups by an oxidative procedure.

The reactions in Schemes 1, 2 and 3 are generally performed whilst the phenolic OH groups are protected with a suitable protecting group (PG). For example, methyl can be used as the protecting group. The PG may be removed in the final step leading to compound 9 (as in Scheme 2) or may be be converted to compound 7 (PG=H) and subsequently compound 8 (PG=H) in the same manner as indicated in Scheme 2.

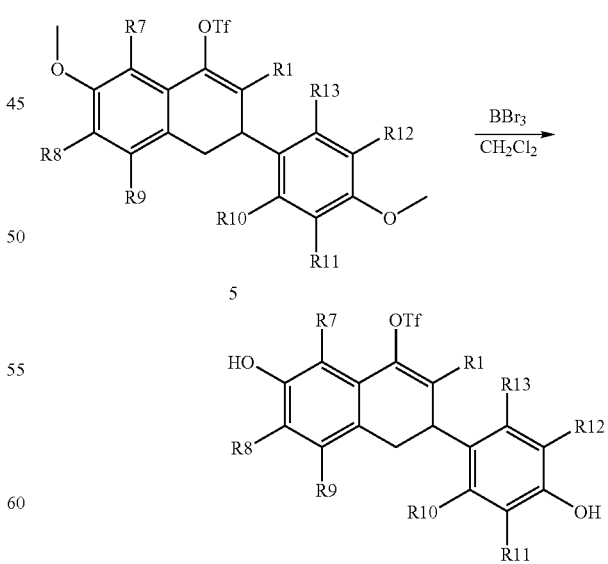

Scheme 4. Preparation of compound 20

The enantiomers of compound 9 may be separated in a conventional way by chiral HPLC using an appropriate chiral HPLC column, for example a Chiralpak AD, OD or AS column, to give single enantiomers 11 and 12, as depicted in Scheme 5.

In an alternative approach, racemic compound 9 is first converted to bis-acetyl compound 10, which is then separated by chiral HPLC to give single enantiomers 21 and 22. Saponification of the acetyl functionalities of compounds 21 and 22, for example by reaction with lithium hydroxide or sodium hydroxide, gives bisphenols 11 (eutomers) and 12 (distomers) as single enantiomers (see Scheme 5).

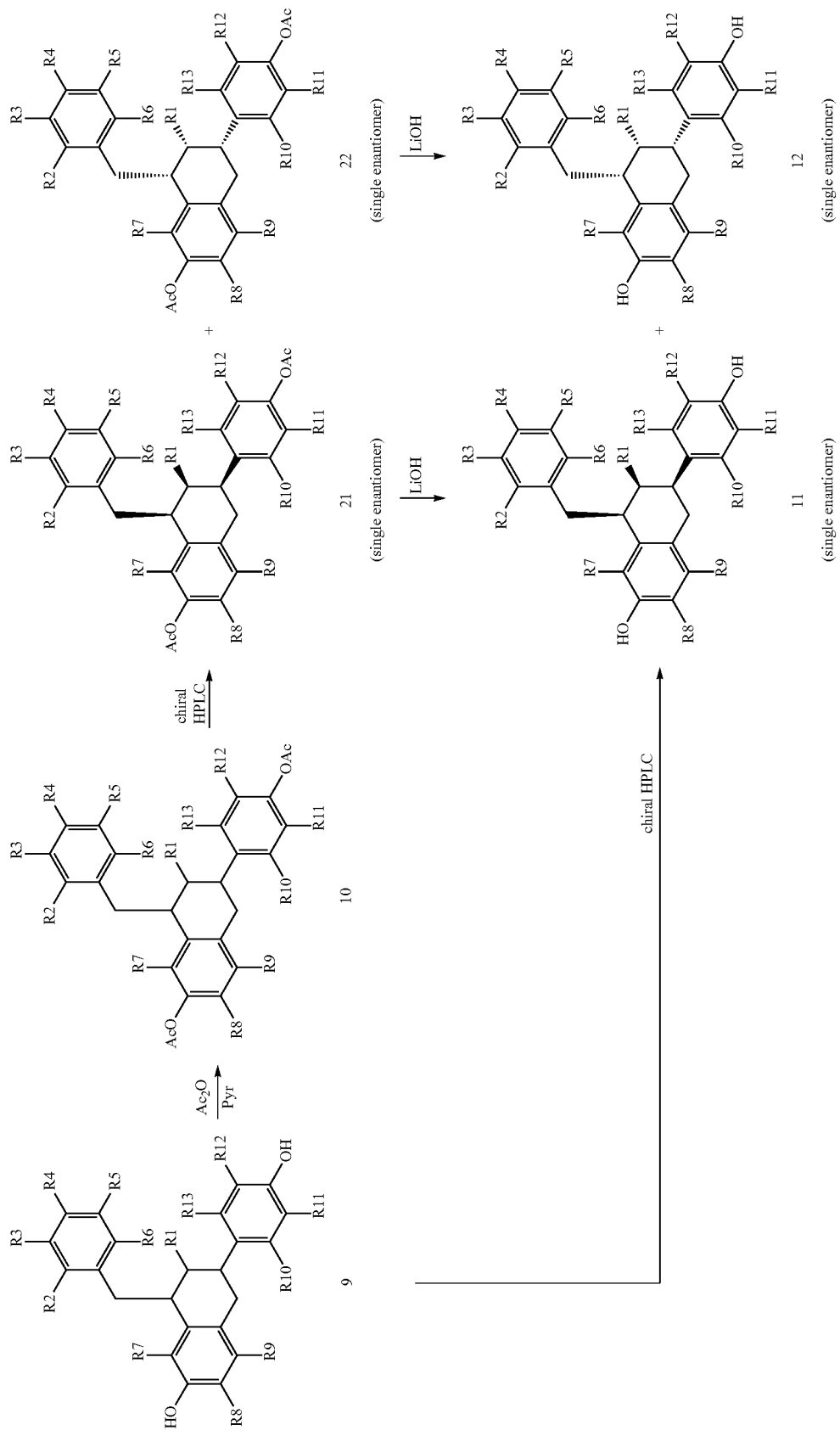

The sequence of reaction steps starting from compound 7 to yield compounds 11 and 12, as indicated in Schemes 2 and 5, may also be altered, in that compound 7 can also first be deprotected to give bisphenolic compound 23, which may then be acetylated to give compound 24, followed by hydrogenation to give compound 10 as a racemate (see Scheme 6).

Ester prodrugs can be made of the parent compounds by esterification of free hydroxyl groups, for example by reaction with an appropriate acid anhydride in pyridine. Thus, compounds 21 and 22 are ester prodrugs of the bisphenols 11 and 12.

The tetrahydronaphthalen-2-ol derivatives of the present invention are selective ERβ agonists (see Table 7 below). The eutomer compounds 11 show the highest receptor activity.

Scheme 6. Alterntive preparation of compound 10

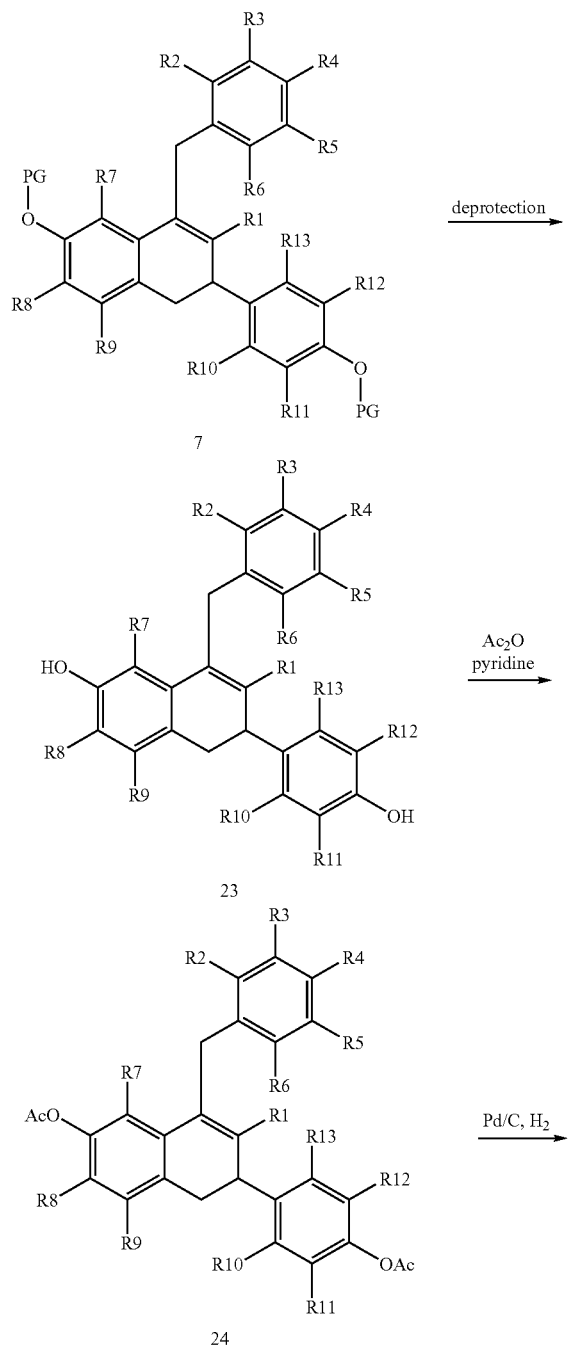

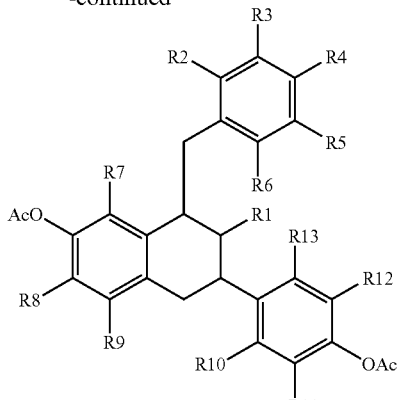

In a further aspect, the tetrahydronaphthalen-2-ol derivatives of the present invention and their prodrugs or isotopically-labelled derivatives thereof are useful in therapy. As such the tetrahydronaphthalen-2-ol derivatives of the present invention are useful for the manufacture of a medicament for the prevention or treatment of lower urinary tract symptoms, benign prostate hyperplasia, prostate cancer, hot flushes, anxiety, depression, breast cancer, medullary thyroid carcinoma, ovarian cancer, inflammatory bowel disease, arthritis, endometriosis, and colon cancer. In one embodiment, the tetrahydronaphthalen-2-ol derivatives of the present invention are useful for the manufacture of a medicament for the prevention or treatment of lower urinary tract symptoms, benign prostate hyperplasia, prostate cancer, breast cancer, medullary thyroid carcinoma, ovarian cancer, endometriosis, and colon cancer. In another embodiment, the tetrahydronaphthalen-2-ol derivatives of the present invention are useful for the manufacture of a medicament for the prevention or treatment of lower urinary tract symptoms, benign prostate hyperplasia, and prostate cancer, more in particular the prevention or treatment of prostate cancer.

The present invention further includes a method for the treatment of a mammal, including a human and an animal, suffering from or liable to suffer from any of the aforementioned diseases or disorders, which comprises administering a therapeutically effective amount of a tetrahydronaphthalen-2-ol derivative according to the present invention or a prodrug or an isotopically-labelled derivative thereof to a mammal in need thereof. By effective amount or therapeutically effective amount is meant an amount of compound or a composition of the present invention effective in inhibiting the above-noted diseases and thus producing the desired therapeutic, ameliorative, inhibitory or preventative effect.

The present invention also relates to a method of preventing or treating lower urinary tract symptoms, benign prostate hyperplasia, prostate cancer, hot flushes, anxiety, depression, breast cancer, medullary thyroid carcinoma, ovarian cancer, inflammatory bowel disease, arthritis, endometriosis, and colon cancer, in particular lower urinary tract symptoms, benign prostate hyperplasia, prostate cancer, breast cancer, medullary thyroid carcinoma, ovarian cancer, endometriosis, and colon cancer, more in particular lower urinary tract symptoms, benign prostate hyperplasia, and prostate cancer, even more particular prostate cancer, comprising administering therapeutically effective amounts of a tetrahydro-naphthalen-2-ol derivative in accordance with the present invention to a mammal in need thereof.

In a still further aspect, the present invention relates to a pharmaceutical composition comprising a tetrahydronaphthalen-2-ol derivative in accordance with the present invention in admixture with a pharmaceutically acceptable excipient. With a pharmaceutically acceptable excipient is meant one or more pharmaceutically acceptable excipients.

The present invention also relates to a method of preventing or treating lower urinary tract symptoms, benign prostate hyperplasia, prostate cancer, hot flushes, anxiety, depression, breast cancer, medullary thyroid carcinoma, ovarian cancer, inflammatory bowel disease, arthritis, endometriosis, and colon cancer, in particular lower urinary tract symptoms, benign prostate hyperplasia, prostate cancer, breast cancer, medullary thyroid carcinoma, ovarian cancer, endometriosis, and colon cancer, more in particular lower urinary tract symptoms, benign prostate hyperplasia, and prostate cancer, even more particular prostate cancer, comprising administering therapeutically effective amounts of a pharmaceutical composition comprising a tetrahydronaphthalen-2-ol derivative in admixture with a pharmaceutically acceptable excipient in accordance with the present invention to a mammal in need thereof.

In a preferred embodiment, the present invention relates to the use of the tetrahydronaphthalen-2-ol derivative of Formula 2 wherein R1 is methyl, R2 is fluorine, and R3-R13 are H (i.e. compound 11a), for the manufacture of a medicament for the prevention or treatment of prostate cancer.

The amount of a tetrahydronaphthalen-2-ol derivative of the present invention, also referred to herein as the active ingredient, which is required to achieve a therapeutic effect will, of course, vary with the particular compound, the route of administration, the age and condition of the recipient and the particular disorder or disease being treated.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.0001-5 mg per kilogram body weight, more in particular 0.001-1 mg per kilogram body weight. The desired dose may be presented as one dose or as multiple subdoses administered at appropriate intervals throughout the day or as doses to be administered at appropriate daily intervals. It may also be administered once-a-week or once-a-month. The dosage as well as the regimen of administration may differ between a female and a male recipient.

Whilst it is possible for the active ingredient to be administered alone, it is preferable to present it as a pharmaceutical composition. The present invention therefore also provides a pharmaceutical composition comprising a tetrahydronaphthalen-2-ol derivative according to the present invention in admixture with one or more pharmaceutically acceptable excipients, such as the ones described in Gennaro et al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, pulmonary, topical (including buccal, sublingual and transdermal), parenteral (including subcutaneous, intravenous and intramuscular) or rectal administration.

The mixtures of a tetrahydronaphthalen-2-ol derivative according to the present invention and one or more pharmaceutically acceptable excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition as described hereinbefore.

The present invention is illustrated in the following examples.

EXAMPLES

In the following examples, the numbering of compounds follows the numbering of compounds shown in Schemes 1 to 6 of the description above.

Example 1

Procedure for the preparation of 2-(3-fluoro-4-methoxybenzyl)-2-(4-methoxy-phenyl)-1,3-dithiane (compound 13a)

General Procedure A (See Scheme 1, Top Panel)

Commercially available 2-(4-methoxyphenyl)-1,3-dithiane 12 (3.94 g, 17.39 mmol) was dissolved in THF (100 ml) to obtain a clear colorless solution. This solution was cooled to −78° C. and then 1.6N n-butyllithium in hexane (10.87 ml, 17.39 mmol) was added to give a yellow solution. The mixture was stirred for 30 min at −78° C. and then 3-fluoro-4-methoxybenzyl bromide (3.81 g, 17.39 mmol) dissolved in THF (50 ml) was added slowly followed by addition of tetramethylethylene-diamine (2.62 ml, 17.39 mmol). This mixture was allowed to reach room temperature in 2 h. Then acetic acid (20 ml) was added and the reaction mixture was stirred at room temperature for 1 h. Water (250 ml) was added, the mixture was extracted with ethyl acetate (2×250 ml) and the combined organic phases were dried with sodium sulfate and concentrated. The crude product was triturated with cold diisopropyl ether to give compound 13a as a white solid (5.94 g, 94% yield). $^1$H NMR (CDCl$_3$): δ 1.85-1.98 (m, 2H), 2.60-2.73 (m, 4H), 3.17 (s, 1H), 3.83 (s, 3H), 3.84 (s, 3H), 6.38 (dd, J1=12 Hz, J2=2.4 Hz, 1H), 6.53 (ddd, J1=9.6 Hz, J2/J3=2.4 Hz, 1H), 6.13 (dd, J1/J2=9.6 Hz, 1H), 7.22 (AB, J1=312 Hz, J2=9.6 Hz, 4H).

Example 2

Procedure for the preparation of 2-(3-fluoro-4-methoxyphenyl)-1-(4-methoxy-phenyl)ethanone (compound 1a)

General Procedure B (See Scheme 1, Top Panel)

Compound 13a (5.94 g, 16.30 mmol) was dissolved in dichloromethane (20 ml) to give a colorless solution. A solution of periodic acid (1.857 g, 8.15 mmol) dissolved in a water/methanol 1:1 mixture (100 ml) was added. The mixture was stirred for 3 h and then sodium hydrogencarbonate (1 g), sodium thiosulfate (1 g) and water (200 ml) were added. This mixture was extracted with ethyl acetate (2×200 ml), the combined organic phases were washed with brine, dried over sodium sulfate and concentrated. The crude product was recrystallized from ethyl acetate/-diisopropyl ether 1:1 (20 ml) to give compound 1a as a white solid (1.98 g, 44% yield). $^1$H NMR (CDCl$_3$): δ 3.87 (s, 3H), 3.88 (s, 3H), 4.16 (s, 2H), 6.88-7.02 (m, 3H), 7.46 (AB, J1=412 Hz, J2=9.6 Hz, 4H).

Example 3

Procedure for the preparation of 1-(2-fluoro-4-methoxyphenyl)-2-(4-methoxy-phenyl)ethanone (compound 1c)

General Procedure C (See Scheme 1, Bottom Panel)

1-Fluoro-3-methoxybenzene (2.243 ml, 19.63 mmol) and 4-methoxyphenylacetyl-chloride (3.00 ml, 19.63 mmol) were dissolved in dichloromethane (50 ml) to obtain a brown solution. Aluminium chloride (3.14 g, 23.56 mmol) was added portion wise and the reaction mixture started refluxing. The mixture was stirred for 2 h at room temperature, poured into ice water (200 ml) and extracted with ethyl acetate (2×250 ml). The combined organic phases were dried with sodium sulfate and concentrated. The crude product was purified by column chromatography (heptane/ethyl acetate 85:15) to give compound 1c as a yellow oil (3.52 g, 65% yield). $^1$H NMR (CDCl$_3$): δ 3.77 (s, 3H), 3.84 (s, 3H), 4.17 (d, J=3 Hz, 2H), 6.60 (dd, J1=13 Hz, J2=2 Hz, 1H), 6.73 (dd, J1=10 Hz, J2=2 Hz, 1H), 7.00 (AB, J1=115 Hz, J2=10 Hz, 4H), 7.87 (dd, J1/J2=10 Hz, 1H).

According to General Procedure C the following compounds were synthesized:

1-(3-Fluoro-4-methoxyphenyl)-2-(4-methoxyphenyl)ethanone (compound 1d) 48% yield. $^1$H NMR (CDCl$_3$): δ 3.78 (s, 3H), 3.94 (s, 3H), 4.16 (s, 2H), 6.97 (dd, J1/J2=9 Hz, 1H), 7.02 (AB, J1=113 Hz, J2=9 Hz, 4H), 7.74 (dd, J1=12 Hz, J2=2 Hz, 1H), 7.79 (ddd, J1=9 Hz, J2/J3=2 Hz, 1H).

1-(4-Methoxy-2-methylphenyl)-2-(4-methoxyphenyl)ethanone (compound 1e) 68% yield. $^1$H NMR (CDCl$_3$): δ 2.23 (s, 3H), 3.77 (s, 3H), 3.87 (s, 3H), 4.16 (s, 2H), 6.83 (d, J1=9 Hz, 1H), 7.02 (AB, J1=121 Hz, J2=9 Hz, 4H), 7.83 (d, J=2 Hz, 1H), 7.87 (dd, J1=9 Hz, J2=2 Hz, 1H).

Example 4

Procedure for the preparation of (E)-3,4-bis-(4-methoxyphenyl)-but-3-enoic acid ethyl ester (compound 2a)

General Procedure D (See Scheme 2)

Commercially available desoxyanisoin (compound 1f, 50.43 g, 197 mmol) and ethyl bromoacetate (49.30 g, 295 mmol) were dissolved in THF (100 ml). The mixture was warmed slightly to obtain a clear colorless solution (solution A). Of this solution 10 ml was added to zinc powder (25.70 g, 394 mmol). This mixture was heated to 85° C. and then iodine (0.499 g, 1.968 mmol) was added carefully, followed by dropwise addition over a 60 min period of the remainder of solution A. The mixture was refluxed for 3 h resulting in a green/grey solution, was allowed to cool to room temperature and was then carefully poured into a cold hydrogen chloride solution (4N, 500 ml). The mixture was extracted with ethyl acetate (2×400 ml) and the combined organic phases were dried with sodium sulfate, and concentrated to give 66.80 g of crude orange oil.

The crude product (66.80 g, 194 mmol) was dissolved in dioxane (100 ml). Hydrogen chloride (6N in isopropanol; 3.23 ml, 19.40 mmol) was added to give an orange solution. The solution was stirred at 80° C. for 2 h. Water (500 ml) was added and the solution was extracted with ethyl acetate (2×300 ml). The combined organic phases were washed with water (3×200 ml), dried with sodium sulfate and concentrated. The crude product was purified by column chromatography (toluene/ethyl acetate 95:5) to give compound 2a as a yellow oil (57.87 g, 91% yield). $^1$H NMR (CDCl$_3$): δ 1.17 (t, J=7 Hz, 3H), 3.68 (s, 2H), 3.82 (2×s, 6H), 4.11 (q, J=7 Hz, 2H), 6.91 (s, 1H), 7.12 (AB, J1=167 Hz, J2=9 Hz, 4H), 7.16 (AB, J1=214 Hz, J2=9 Hz, 4H).

According to General Procedure D the following compounds were synthesized:

Ethyl 3-(3-fluoro-4-methoxyphenyl)-4-(4-methoxyphenyl)but-3-enoate (compound 2b)

42% yield. $^1$H NMR (CDCl$_3$): δ 1.19 (t, J=7 Hz, 3H), 3.65 (s, 2H), 4.13 (q, J=7 Hz, 2H), 7.12 (AB, J1=160 Hz, J2=10 Hz, 4H).

Ethyl 3-(2-fluoro-4-methoxyphenyl)-4-(4-methoxyphenyl)but-3-enoate (compound 2c)

69% yield. $^1$H NMR (CDCl$_3$): δ 1.16 (t, J=7 Hz, 3H), 3.67 (s, 2H), 3.78 (s, 3H), 3.80 (s, 3H), 4.07 (q, J=7 Hz, 2H).

Example 5

Procedure for the preparation of ethyl 3,4-bis(4-methoxyphenyl)-2-methyl-butanoate (compound 3a)
General Procedure E (See Scheme 2)

Diisopropylamine (8.24 g, 81 mmol) was dissolved in tetrahydrofuran (100 ml). The solution was cooled to −50° C. and 1.6N n-butyllithium in hexane (50.9 ml, 81 mmol) was added slowly. This mixture was stirred for 30 min and then cooled to −78° C. (solution A). Compound 2 (26.59 g, 81 mmol) was dissolved in tetrahydrofuran (150 ml) and was added drop wise over a period of 30 min to solution A. The yellow reaction mixture was stirred for 30 min at −78° C.

Iodomethane (57.8 g, 407 mmol) was added and the mixture was allowed to reach room temperature within 3 h. The reaction was completed (checked with NMR because the starting material and product have the same Rf). Water (200 ml) and ethyl acetate (100 ml) were added to the reaction mixture and the separated organic phase was washed with water (100 ml) and dried over sodium sulfate, filtered and concentrated to give the crude intermediate as a brown oil (28.0 g, 101%).

The crude intermediate was dissolved in ethyl acetate (250 ml) and acetic acid (0.494 g, 8.23 mmol) and palladium (10% on activated carbon; 0.974 g, 8.23 mmol) was added to give a black suspension. Hydrogen was bubbled through the reaction mixture for 48 h. The mixture was filtered over decalite. The filtrate was concentrated to give the crude compound (mixture of diastereoisomers) as a yellow oil (27.0 g, 79 mmol, 96% yield). $^1$H NMR (CDCl$_3$): δ 0.93 (d, J=6.7 Hz, 3H), 1.03 (t, J=7 Hz, 3H), 1.28 (d, J=7 Hz, 6H), 3.75 (4×s, 6H), 3.90 (q, J=7 Hz, 2H).

According to General Procedure E the following compounds were synthesized:

Ethyl 2-ethyl-3,4-bis(4-methoxyphenyl)-butanoate (compound 3b) 97% yield. $^1$H NMR (CDCl$_3$): δ 1.67-1.88 (m, 2H), 3.70-3.78 (4×s, 6H), 6.62-6.95 (m, 8H).

Ethyl 3,4-bis(4-methoxyphenyl)-2-propylbutanoate (compound 3c) 62% yield. $^1$H NMR (CDCl$_3$): δ 3.64-3.69 (4×s, 6H), 6.57-6.99 (m, 8H).

Ethyl 2-ethyl-3-(3-fluoro-4-methoxyphenyl)-4-(4-methoxyphenyl)butanoate (compound 3d) 38% yield. $^1$H NMR (CDCl$_3$): δ 1.79 (m, 2H), 2.58 (m, 1H), 2.74 (dd, J1=10 Hz, J2=13 Hz, 1H), 2.95 (m, 1H), 3.11 (dd, J1=56 Hz, J2=13 Hz, 1H), 3.88 (m, 3H), 4.12 (q, J=7 Hz, 3H), 6.64-6.95 (m, 7H).

Ethyl 2-ethyl-3-(2-fluoro-4-methoxyphenyl)-4-(4-methoxyphenyl)butanoate (compound 3e) 69% yield. $^1$H NMR (CDCl$_3$): δ 1.78 (m, 2H), 2.7 (m, 2H), 6.42-6.70 (m, 7H).

Example 6

Procedure for the preparation of ethyl 4-(3-fluoro-4-methoxyphenyl)-3-(4-methoxyphenyl)-2-methylbutanoate (compound 3f)

General Procedure F (See Scheme 3)

Commercially available zinc (1.892 g, 28.9 mmol) was suspended in THF (25 ml).

Diisobutylaluminium hydride (0.598 ml, 0.723 mmol) was added and the suspension was stirred for 15 min, then compound 1a (1.984 g, 7.23 mmol) was added and the reaction temperature was brought to 60° C. Ethyl-2-bromopropionate (1.879 ml, 14.47 mmol) was added and after a while the reaction became exothermic and the temperature increased until reflux. This mixture was stirred at reflux for 2 h and then cooled to room temperature. 4N HCl (100 ml) was added and the mixture was stirred for 5 min and then extracted with ethyl acetate (2×100 ml). The organic layers were combined and washed with 4N HCl (2×100 ml), water, dried over sodium sulfate and concentrated to give a yellow oil (2.8 g, 103% crude yield).

This crude product (2.8 g, 7.44 mmol) and hydrogen chloride (6N in isopropanol; 0.595 ml, 2.98 mmol) were dissolved in dioxane (20 ml) to give an orange solution. The solution was stirred at 90° C. for 4 h. The solution was concentrated to give the crude intermediate (2.08 g, 78% yield) as a red oil. This stilbene derivative (2.08 g, 5.80 mmol) was dissolved in ethyl acetate (30 ml) to give an orange solution. This solution was degassed and then palladium on activated carbon (0.069 g, 0.580 mmol) and acetic acid (0.033 ml, 0.580 mmol) were added to give a black suspension. Hydrogen was bubbled through the reaction mixture for 3 h. The mixture was filtered over decalite. The filtrate was concentrated to give the crude compound (mixture of diastereoisomers) as a yellow oil (2.02 g, 97% yield). $^1$H NMR (CDCl$_3$): δ 1.04 (t, J=7 Hz, 3H), 1.27 (d, J=7 Hz, 3H), 2.75-3.10 (m, 4H), 3.75-3.81 (4×s, 6H), 4.19 (q, J=7 Hz, 2H), 6.56-7.08 (m, 7H).

According to General Procedure F the Following Compound was Synthesized:

Ethyl 3-(4-methoxy-3-methylphenyl)-4-(4-methoxyphenyl)-2-methylbutanoate (compound 3g) 71% yield. $^1$H NMR (CDCl$_3$): δ 1.05 (t, J=7 Hz, 3H), 1.24 (d, J=7 Hz, 3H), 2.65-3.10 (m, 4H), 3.72-3.78 (4×s, 6H), 4.17 (q, J=7 Hz, 2H), 6.62-6.97 (m, 7H).

Example 7

Procedure for the preparation of 7-methoxy-3-(4-methoxyphenyl)-2-methyl-3,4-dihydronaphthalen-1(2H)-one (compound 4a)

General Procedure G (see Scheme 2)

Compound 3a (27.0 g, 79 mmol) was dissolved in methanesulfonic acid (100 ml) which gave a black solution. The mixture was heated (90° C.) for 1 h and then allowed to reach room temperature. The solution was poured into water (500 ml) and the mixture was extracted with ethyl acetate (2×250 ml). The combined organic phases were washed with water (2×200 ml) dried with sodium sulfate and concentrated. The crude product was purified by column chromatography (toluene/ethyl acetate 98:2) to give compound 4a as a yellow oil (13.4 g, 57% yield). $^1$H NMR (CDCl$_3$): δ 1.06 (d, J=7 Hz, 3H), 2.72-3.23 (m, 2H), 3.33 (dd, J1=17 Hz, J2=10 Hz, 1H), 3.57 (m, 1H), 3.79-3.86 (s, 6H), 6.83-6.92 (m, 2H), 7.06-7.22 (m, 4H), 7.54-7.57 (m, 1H).

According to General Procedure G the following compounds were synthesized:

2-Ethyl-7-methoxy-3-(4-methoxyphenyl)-3,4-dihydronaphthalen-1(2H)-one (compound 4b) 59% yield. $^1$H NMR (CDCl$_3$): δ 0.78-0.92 (m, 3H), 1.34-1.55 (m, 2H), 1.90-2.00 (m, 1H), 2.62-3.65 (m, 3H), 3.78-3.86 (m, 6H), 6.81-6.90 (m, 2H), 7.05-7.21 (m, 4H), 7.54-7.57 (m, 1H).

7-Methoxy-3-(4-methoxyphenyl)-2-propyl-3,4-dihydronaphthalen-1(2H)-one (compound 4c) 89% yield. $^1$H NMR (CDCl$_3$): δ 0.73-0.87 (m, 3H), 1.14-1.78 (m, 5H), 2.72-3.65 (m, 3H), 3.78-3.87 (m, 6H), 6.81-6.90 (m, 2H), 7.05-7.22 (m, 4H), 7.54-7.57 (m, 1H).

2-Ethyl-3-(2-fluoro-4-methoxyphenyl)-7-methoxy-3,4-dihydronaphthalen-1(2H)-one (compound 4d) 100% yield. This compound was used without purification in the next synthetic step.

3-(2-Fluoro-4-methoxyphenyl)-7-methoxy-2-methyl-3,4-dihydronaphthalen-1(2H)-one (compound 4e) 100% yield. $^1$H NMR (CDCl$_3$): δ 0.78-0.92 (m, 3H), 2.83-3.50 (m, 3H), 3.78-3.85 (m, 6H), 6.59-6.73 (m, 2H), 7.00-7.21 (m, 3H), 7.50-7.59 (m, 1H).

2-Ethyl-3-(3-fluoro-4-methoxyphenyl)-7-methoxy-3,4-dihydronaphthalen-1(2H)-one (compound 4f) 53% yield. $^1$H NMR (CDCl$_3$): δ 0.80-0.91 (m, 3H), 1.35-1.70 (m, 2H), 2.63-3.35 (m, 3H), 3.81-3.92 (m, 6H), 6.83-7.26 (m, 6H), 7.54-7.57 (m, 1H).

7-Methoxy-3-(4-methoxy-3-methylphenyl)-2-methyl-3,4-dihydronaphthalen-1(2H)-one (compound 4g) 53% yield. $^1$H NMR (CDCl$_3$): δ 1.02 (d, J=8 Hz, 3H), 2.28 (s, 3H), 3.81-3.87 (m, 6H), 6.75-7.24 (m, 5H), 7.54-7.57 (dd, J1=10 Hz, J2=3 Hz, 1H).

8-Fluoro-7-methoxy-3-(4-methoxyphenyl)-2-methyl-3,4-dihydronaphthalen-1(2H)-one (compound 4h) 124% crude yield. $^1$H NMR (CDCl$_3$): δ 1.02 (d, J=8 Hz, 3H), 2.70-3.60 (m, 4H), 3.78-3.94 (m, 6H), 6.73-7.18 (m, 6H), 7.66 (dd, J1=J2=8 Hz, 1H).

Example 8

Procedure for the preparation of 7-methoxy-3-(4-methoxyphenyl)-2-methyl-3,4-dihydronaphthalen-1-yl trifluoromethanesulfonate (compound 5a)

General Procedure H (See Scheme 2)

Compound 4a (13.00 g, 43.9 mmol) and 2,6-di-tert-butyl-4-methylpyridine (20.98 g, 110 mmol) and trifluoromethanesulfonic anhydride (24.75 g, 88 mmol) were dissolved in dichloromethane (200 ml) to give a brown solution. The reaction was stirred for 16 h under N$_2$ at room temperature and checked with TLC. The reaction mixture was diluted with dichloromethane (150 ml) and the organic phase was washed twice with 2N HCl (200 ml), water (200 ml) and concentrated. The crude brown oil was purified by silica gel chromatography (heptane/ethyl acetate 9/1) to give compound 5a as a yellow oil (15.04 g, 82%). $^1$H NMR (CDCl$_3$): δ 1.87 (s, 3H), 2.84 (dd, J1=15, J2=5 Hz, 1H), 3.29 (dd, J1=15 Hz, J2=7 Hz, 1H), 3.60 (dd, J1 =5 Hz, J2=7 Hz, 1H), 3.75 (s, 3H), 3.82 (s, 3H), 6.73 (dd, J1=9 Hz, J2=2 Hz, 1H), 6.86 (AB, J1=84 Hz, J2=18 Hz, 4H), 6.93 (d, J=9 Hz, 1H).

According to General Procedure H the following compounds were synthesized:

7-Methoxy-3-(4-methoxyphenyl)-2-ethyl-3,4-dihydronaphthalen-1-yl trifluoromethanesulfonate (compound 5b) 89% yield. $^1$H NMR (CDCl$_3$): δ 1.06 (t, J=8 Hz, 3H), 2.05 (m, 1H), 2.55 (m, 1H), 2.82 (dd, J1=15 Hz, J2=3 Hz, 1H), 3.29 (dd, J1=15 Hz, J2=7 Hz, 1H), 3.73 (s, 3H), 3.82 (s, 3H), 6.69-7.00 (Ar, 7H).

7-Methoxy-3-(4-methoxyphenyl)-2-propyl-3,4-dihydronaphthalen-1-yl trifluoromethanesulfonate (compound 5c) 81% yield. $^1$H NMR (CDCl$_3$): δ 0.78 and 0.90 (2×t, 3H), 3.73-3.85 (6×s, 6H), 6.69-7.20 (Ar, 7H).

2-Ethyl-3-(2-fluoro-4-methoxyphenyl)-7-methoxy-3,4-dihydronaphthalen-1-yl trifluoromethanesulfonate (compound 5d) 64% yield. $^1$H NMR (CDCl$_3$): δ 1.01-1.17 (m, 3H), 2.04 (m, 1H), 2.55 (m, 1H), 2.82 (m, 1H), 3.21 (m, 1H), 3.73-3.87 (m, 6H), 6.36-7.00 (Ar, 6H).

3-(2-Fluoro-4-methoxyphenyl)-7-methoxy-2-methyl-3,4-dihydronaphthalen-1-yl trifluoromethanesulfonate (compound 5e) 63% yield. $^1$H NMR (CDCl$_3$): δ 1.87 (s, 3H), 2.84 (m, 1H), 3.21 (m, 1H), 3.73-3.84 (s, 6H), 4.05 (m, 1H), 6.42-6.98 (m, 6H).

2-Ethyl-3-(3-fluoro-4-methoxyphenyl)-7-methoxy-3,4-dihydronaphthalen-1-yl trifluoromethanesulfonate (compound 5f) 53% yield. $^1$H NMR (CDCl$_3$): δ 1.07 (t, J=7 Hz, 3H), 2.07, 2.54 (m, 1H), 2.80 (dd, J1=15 Hz, J2=3 Hz, 1H), 3.21 (dd, J1=15 Hz, J2=7 Hz, 1H), 3.73 (dd, J1=3 Hz, J2=7 Hz, 1H), 3.82 (s, 6H), 6.71-7.13 (Ar, 6H).

7-Methoxy-3-(4-methoxy-3-methylphenyl)-2-methyl-3,4-dihydronaphthalen-1-yl trifluoromethanesulfonate (compound 5g) 36% yield $^1$H NMR (CDCl$_3$): δ 1.87 (s, 3H), 2.84 (dd, J1=5 Hz, J2=15 Hz, 1H), 3.27 (dd, J1=7 Hz, J2=15 Hz, 1H), 3.56 (dd, J1=5 Hz, J2=7 Hz, 1H), 3.76 (s, 3H), 3.83 (s, 3H), 4.05 (m, 1H), 6.64-7.01 (m, 6H).

8-Fluoro-7-methoxy-3-(4-methoxyphenyl)-2-methyl-3,4-dihydronaphthalen-1-yl trifluoromethanesulfonate (compound 5h) 42% yield. $^1$H NMR (CDCl$_3$): δ 1.87 (s, 3H), 2.80 (dd, J1=5 Hz, J2=15 Hz, 1H), 3.29 (dd, J1=7 Hz, J2=15 Hz, 1H), 3.58 (dd, J1=5 Hz, J2=7 Hz, 1H), 3.76 (s, 3H), 3.91 (s, 3H), 6.74-7.14 (m, 6H).

Example 9

Procedure for the preparation of 7-hydroxy-3-(4-hydroxyphenyl)-2-methyl-3,4-di-hydronaphthalen-1-yl trifluoromethanesulfonate (compound 20) (see Scheme 4)

Compound 5a (0.315 g, 0.735 mmol) was dissolved in dichloromethane (5 ml) to obtain a clear colorless solution. This solution was cooled to 0° C. and then boron tribromide (0.283 ml, 2.94 mmol) was added carefully to give a brown solution. The mixture was stirred at room temperature for 2 h and then poured into ice water (25 ml) and extracted with dichloromethane (2×10 ml). The organic phases were combined, washed with a saturated sodium bicarbonate solution (50 ml) and water (50 ml), dried with sodium sulfate and concentrated. The crude product was purified by column chromatography (toluene/ethyl acetate 90:10) to give compound 20 as a yellow oil (0.206 g, 70% yield). $^1$H NMR (CDCl$_3$): δ 1.86 (s, 3H), 2.80 (dd, J1=5 Hz, J2=16 Hz, 1H), 3.26 (dd, J1=7 Hz, J2=16 Hz, 1H), 3.57 (dd, J1=5 Hz, J2=7 Hz, 1H), 6.66 (dd, J1=2 Hz, J2=8 Hz, 1H), 6.79 (AB, J1=10 Hz, J2=90 Hz, 4H).

Example 10

Procedure for the preparation of 4-(2-fluorobenzyl)-6-methoxy-2-(4-methoxy-phenyl)-3-methyl-1,2-dihydronaphthalene (compound 7a)
General Procedure I (See Scheme 2)

Compound 5a (35.00 g, 82 mmol) was dissolved in THF (400 ml) to obtain a clear colorless solution. This solution was degassed and then 1,1'-bis(diphenyl-phosphino)ferrocene palladium (II) chloride dichloromethane (3.30 g, 4.08 mmol) and 2-fluorobenzylzinc chloride (327 ml, 163 mmol) were added to give a brown solution. The mixture was refluxed overnight, was allowed to cool to room temperature and was then poured into a saturated ammonium chloride solution (500 ml). The mixture was extracted with ethyl acetate (2×300 ml) and the combined organic phases were dried with sodium sulfate and concentrated. The crude product was purified by column chromatography (heptane/ethyl acetate 8:2) to give compound 7a as a yellow oil (29.6 g, 93% yield). $^1$H NMR (CDCl$_3$): see table.

According to General Procedure I the compounds in Table 1 were synthesized:

TABLE 1

Compounds prepared according to General Procedure I

| Compound | Name | Structure | Yield | $^1$H NMR |
|---|---|---|---|---|
| 7a | 4-(2-fluorobenzyl)-6-methoxy-2-(4-methoxyphenyl)-3-methyl-1,2-dihydronaphthalene | 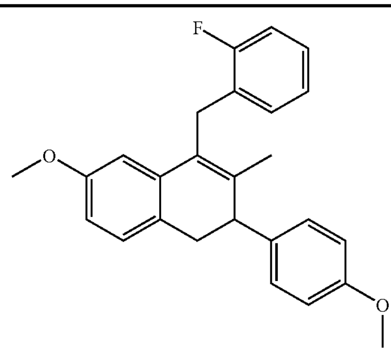 | 93% | $^1$H NMR (CDCl$_3$): δ 1.84 (s, 3H), 2.82 (dd, J1 = 15 Hz, J2 = 4 Hz, 1H), 3.28 (dd, J1 = 15 Hz, J2 = 8 Hz, 1H), 3.46 (dd, J1 = 8 Hz, J2 = 4 Hz, 1H), 3.67 (s, 3H), 3.73 (s, 3H), 3.95 (q, J = 17 Hz, 2H), 6.57 (dd, J1 = 9 Hz, J2 = 2 Hz, 1H), 6.72 (s, 1H), 6.87 (d, J = 9 Hz, 1H), 6.88 (AB, J1 = 113 Hz, J2 = 9 Hz, 4H), 6.93-7.17 (m, 4H) |

TABLE 1-continued

Compounds prepared according to General Procedure I

| Compound | Name | Structure | Yield | ¹H NMR |
|---|---|---|---|---|
| 7b | 4-(2-fluorobenzyl)-6-methoxy-2-(4-methoxyphenyl)-3-ethyl-1,2-dihydronaphthalene | 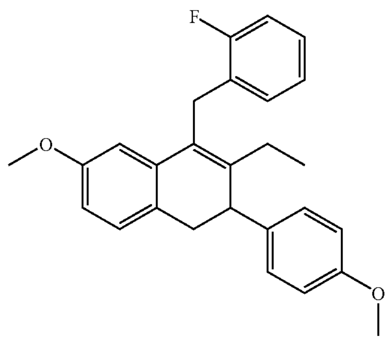 | 100% (‡) | ¹H NMR (CDCl$_3$): δ 1.05 (t, J = 7 Hz, 3H), 2.06 (m, 1H), 2.54 (m, 1H), 2.82 (dd, J1 = 3Hz, J2 = 16Hz, 1H), 3.29 (dd, J1 = 16 Hz, J2 = 7 Hz, 1H), 3.73 (s, 3H), 3.81 (s, 3H), 3.97 (AB, J = 16 Hz, J = 36 Hz, 2H), 6.83 (AB, J1 = 8 Hz, J2 = 84 Hz, 4H), 6.90 (d, J = 8 Hz, 1H). |
| 7c | 4-(2-fluorobenzyl)-6-methoxy-2-(4-methoxyphenyl)-3-propyl-1,2-dihydronaphthalene | 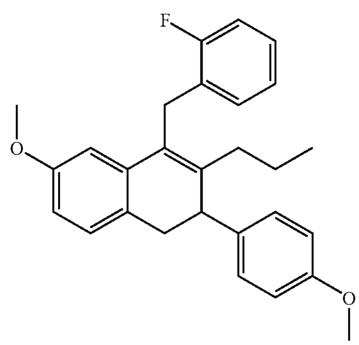 | 62% | ¹H NMR (CDCl$_3$): δ 0.90 (t, 3H), 1.49 (m, 2H), 1.89 (m, 1H), 2.35(m, 1H), 2.83 (dd, J1 = 2 Hz, J2 = 15 Hz, 1H), 3.28 (dd, J1 = 7 Hz, J2 = 15 Hz, 1H), 3.67 (s, 3H), 3.73 (s, 3H), 3.95 (AB, J = 16 Hz, J = 41 Hz, 2H), 6.56 (dd, J1 = 9 Hz, J2= 3 Hz, 1H), 6.71-6.99 (AB, J1 = 109 Hz, J2 = 9 Hz, 4H). |
| 7d | 4-benzyl-6-methoxy-2-(4-methoxyphenyl)-3-methyl-1,2-dihydronaphthalene | 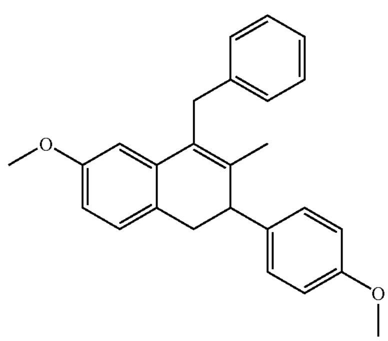 | 84% | ¹H NMR (CDCl$_3$): δ 1.87 (s, 3H), 2.81 (dd, J1 = 4 Hz, J2 = 15 Hz, 1H), 3.28 (dd, J1 = 15 Hz, J2 = 8 Hz, 1H), 3.46 (dd, J1 = 8 Hz, J2 = 4 Hz, 1H), 3.66 (s, 3H), 3.74 (s, 3H), 3.95 (AB, J = 17 Hz, J = 55 Hz, 2H), 6.66 (dd, J1 = 8 Hz, J2 = 3 Hz, 1H), 6.78 (d, J = 3 Hz, 1H), 6.86 (AB, J1 = 9 Hz, J2 = 114 Hz, 4H), 6.87 (d, J = 8 Hz, 1H), 7.14-7.35 (m, 5H). |
| 7e | 4-benzyl-3-ethyl-6-methoxy-2-(4-methoxyphenyl)-1,2-dihydronaphthalene | 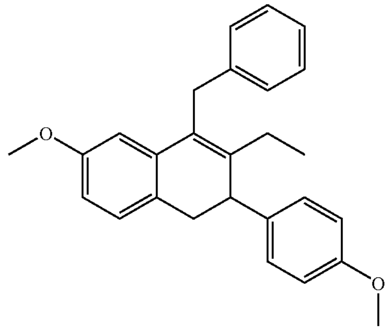 | 100% | ¹H NMR (CDCl$_3$): δ 1.05 (t, J = 8 Hz, 3H), 1.92 (m, 1H), 2.44 (m, 1H), 2.83 (dd, J1 = 3 Hz, J2 = 15 Hz, 1H), 3.27 (dd, J1 = 15 Hz, J2 = 8 Hz, 1H), 3.58 (dd, J1 = 3Hz, J2 = 8 Hz, 1H), 3.64 (s, 3H), 3.73 (s, 3H), 3.97 (AB, J = 16 Hz, J = 65 Hz, 2H), 6.55 (dd, J1 = 8 Hz, J2 = 3 Hz, 1H), 6.75 (d, J = 3 Hz, 1H), 6.84 (d, J = 8 Hz, 1H), 6.85 (AB, J1 = 8 Hz, J2 = 117 Hz, 4H), 7.18-7.38 (m, 4H). |

TABLE 1-continued

Compounds prepared according to General Procedure I

| Compound | Name | Structure | Yield | ¹H NMR |
|---|---|---|---|---|
| 7f | 4-(3-fluorobenzyl)-6-methoxy-2-(4-methoxyphenyl)-3-methyl-1,2-dihydronaphthalene | 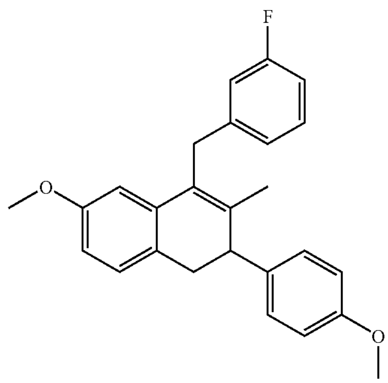 | 93% | ¹H NMR (CDCl$_3$): δ 1.84 (s, 3H), 2.82 (dd, J2 = 15 Hz, J2 = 4 Hz, 1H), 3.28 (dd, J2 = 15 Hz, J2 = 8 Hz, 1H), 3.46 (dd, J1 = 8 Hz, J2 = 4 Hz, 1H), 3.67 (s, 3H), 3.73 (s, 3H), 3.95 (AB, J = 17 Hz, J = 46 Hz, 2H), 6.57 (dd, J1 = 9 Hz, J2 = 2 Hz, 1 H), 6.72 (s, 1H), 6.88 (AB, J1 = 107 Hz, J2 = 9 Hz, 4H). |
| 7g | 4-(4-fluorobenzyl)-6-methoxy-2-(4-methoxyphenyl)-3-methyl-1,2-dihydronaphthalene | 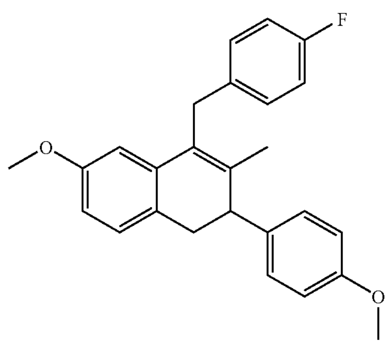 | 75% | ¹H NMR (CDCl$_3$): δ 1.84 (s, 3H), 2.82 (dd, J1 = 15 Hz, J2 = 4 Hz, 1H), 3.27 (dd, J1 = 15 Hz, J2 = 8 Hz, 1H), 3.45 (dd, J1 = 8 Hz, J2 = 4 Hz, 1H), 3.67 (s, 3H), 3.74 (s, 3H), 3.91 (AB, J = 16 Hz, J = 46 Hz, 2H), 6.57 (dd, J1 = 9 Hz, J2 = 2 Hz, 1 H), 6.72 (s, 1H), 6.87 (d, J = 9 Hz, 1H), 6.88 (AB, J1 = 105 Hz, J2 = 9 Hz, 4H), 6.95 (dd, J1,2 = 9 Hz, 2H), 7.19 (m, 2H). |
| 7h | 4-(2,5-difluorobenzyl)-6-methoxy-2-(4-methoxyphenyl)-3-methyl-1,2-dihydronaphthalene | 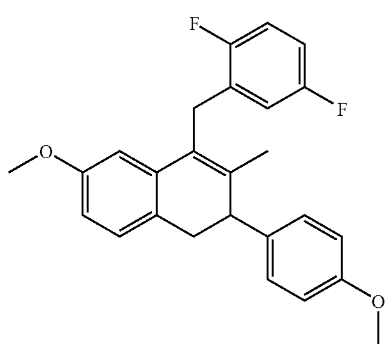 | 52% | ¹H NMR (CDCl$_3$): δ 1.83 (s, 3H), 2.83 (dd, J1 = 15 Hz, J2 = 4 Hz, 1H), 3.29 (dd, J1 = 15 Hz, J2 = 8 Hz, 1H), 3.47 (dd, J1 = 8 Hz, J2 = 4 Hz, 1H), 3.71 (s, 3H), 3.74 (s, 3H), 3.93 (AB, J = 18 Hz, J = 40 Hz, 2H), 6.59 (dd, J1 = 9 Hz, J2 = 2 Hz, 1 H), 6.72 (d, J = 4H), 6.87 (d, J = 9 Hz, 1H), 6.88 (AB, J1 = 107 Hz, J2 = 9 Hz, 4H), 690 (d, J = 9 Hz, 1 H). |
| 7i | 4-(2,6-difluorobenzyl)-6-methoxy-2-(4-methoxyphenyl)-3-methyl-1,2-dihydronaphthalene | 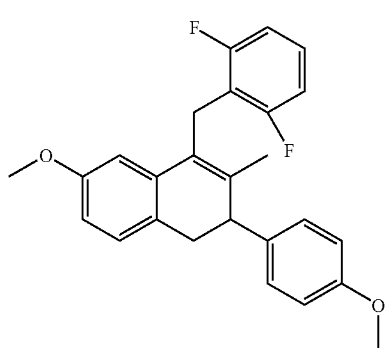 | 89% | ¹H NMR (CDCl$_3$): δ 1.96 (s, 3H), 2.71 (dd, J1 = 4 Hz, J2 = 14 Hz, 1H), 3.18 (dd, J1 = 16 Hz, J2 = 8 Hz, 1H), 3.43 (dd, J1 = 4 Hz, J2 = 8 Hz, 1H), 3.73 (s, 3H), 3.75 (s, 3H), 4.03 (AB, J = 17 Hz, J = 28 Hz, 2H), 6.54 (dd, J1 = 9 Hz, J2 = 3 Hz, 1H), 6.83 (AB, J1 = 9 Hz, J2 = 106 Hz, 4H), 6.99 (d, J = 3 Hz, 1H). |

TABLE 1-continued

Compounds prepared according to General Procedure I

| Compound | Name | Structure | Yield | ¹H NMR |
|---|---|---|---|---|
| 7j | 2-((7-methoxy-3-(4-methoxyphenyl)-2-methyl-3,4-dihydronaphthalen-1-yl)methyl)benzonitrile | 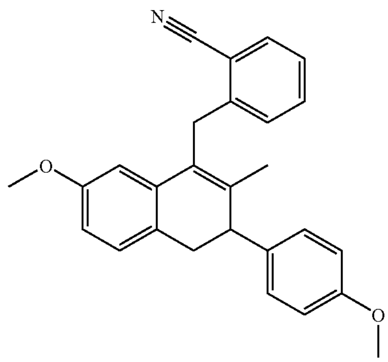 | 90% | ¹H NMR (CDCl$_3$): δ 1.84 (s, 3H), 2.85 (dd, J1 = 4 Hz, J2 = 15 Hz, 1H), 3.31 (dd, J1 = 15 Hz, J2 = 7 Hz, 1H), 3.49 (dd, J1 = 4 Hz, J2 = 7 Hz, 1H), 3.69 (s, 3H), 3.75 (s, 3H), 4.18 (AB, J1 = 19 Hz, J2 = 37 Hz, 2H), 6.59 (dd, J1 = 2 Hz, J2 = 8 Hz, 1H), 6.64 (d, J = 8 Hz, 1H)., 6.89 (AB, J1= 9 Hz, J2 = 105 Hz, 4H), 6.91 (d, J = 8 Hz, 1H), 7.16-7.68 (m, 4H). |
| 7k | 2-((7-methoxy-3-(4-methoxyphenyl)-2-ethyl-3,4-dihydronaphthalen-1-yl)methyl)benzonitrile | 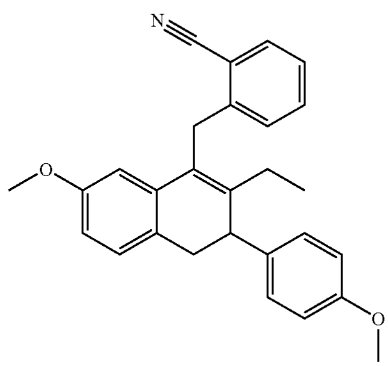 | 31% | ¹H NMR (CDCl$_3$): δ 1.04 (t, J = 7 Hz, 3H), 1.96 (m, 1H), 2.36 (m, 1H), 2.87 (dd, J1 = 3 Hz, J2 = 15 Hz, 1H), 3.30 (dd, J1 = 15 Hz, J2 = 8 Hz, 1H), 3.60 (dd, J1 = 3 Hz, J2 = 8 Hz, 1H), 3.68 (s, 3H), 3.74 (s, 3H), 4.20 (AB, J = 18 Hz, J = 38 Hz, 2H), 6.57 (dd, J1 = 8 Hz, J2 = 3 Hz, 1H), 6.60 (d, J = 3 Hz, 1H), 6.87 (AB, J2 = 9 Hz, J2 = 109 Hz, 4H), 6.88 (d, J = 8 Hz, 1H), 7.20-7.68 (m, 4H). |
| 7l | 4-(2-chlorobenzyl)-6-methoxy-2-(4-methoxyphenyl)-3-methyl-1,2-dihydronaphthalene | 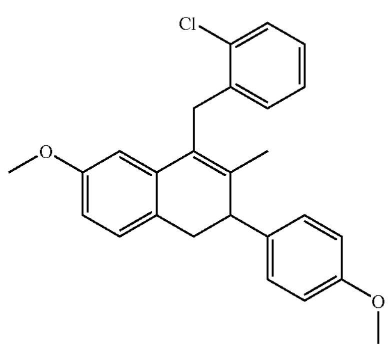 | 20% | ¹H NMR (CDCl$_3$): δ 1.81 (s, 3H), 2.85 (dd, J1 = 4 Hz, J2 = 16 Hz, 1H), 3.31 (dd, J1 = 16 Hz, J2 = 8 Hz, 1H), 3.48 (dd, J1 = 4 Hz, J2 = 8 Hz, 1H), 3.67 (s, 3H), 3.75 (s, 3H), 4.01 (AB, J1 = 18 Hz, J2 = 37 Hz, 2H), 6.58 (dd, J1 = 3 Hz, J2 = 8 Hz, 1H), 6.61 (d, J = 3 Hz, 1H)., 6.89 (AB, J1 = 9 Hz, J2 = 113 Hz, 4H), 6.91 (d, J = 8 Hz, 1H). |
| 7m | 3-ethyl-6-methoxy-4-(4-methoxybenzyl)-2-(4-methoxyphenyl)-1,2-dihydronaphthalene | 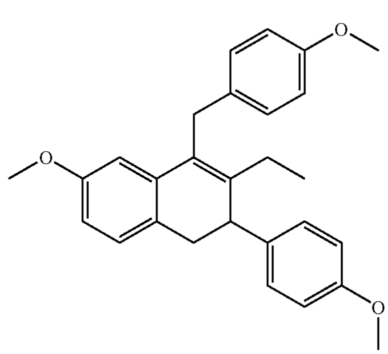 | 99% | ¹H NMR (CDCl$_3$): δ 1.05 (t, J = 7 Hz, 3H), 1.91 (m, 1H), 2.43 (m, 1H), 2.82 (dd, J1 = 2 Hz, J2 = 14 Hz, 1H), 3.26 (dd, J1 = 14 Hz, J2 = 8 Hz, 1H), 3.56 (dd, J1 = 2 Hz, J2 = 8 Hz, 1H), 3.67 (s, 3H), 3.73 (s, 3H), 3.81 (s, 3H), 3.90 (AB, J = 17 Hz, J = 65 Hz, 2H), 6.54 (dd, J1 = 8 Hz, J2 = 3 Hz, 1H), 6.77 (d, J = 3 Hz, 1H), 6.81 (d, J = 8 Hz, 1H), 6.84 (AB, J1 = 9 Hz, J2 = 116 Hz, 4H), 7.09 (AB, J1 = 9 Hz, J2 = 162 Hz, 4H). |

TABLE 1-continued

Compounds prepared according to General Procedure I

| Compound | Name | Structure | Yield | ¹H NMR |
|---|---|---|---|---|
| 7n (§) | 6-(4-hydroxyphenyl)-8-(2-methoxybenzyl)-7-methyl-5,6-dihydronaphthalen-2-ol | 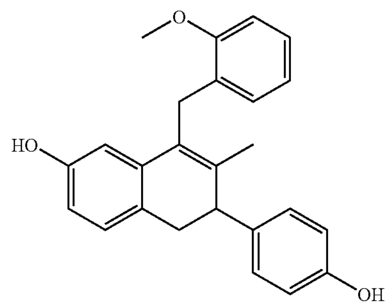 | 56% | ¹H NMR (CDCl$_3$): δ 1.78 (s, 3H), 2.80 (m, 1H), 3.24 (m, 1H), 3.40 (m, 1H), 3.85 (AB, J1 = 17 Hz, J2 = 38 Hz, 2H), 3.90 (s, 3H), 6.30-719 (m, 11H). |
| 7o | 3-ethyl-2-(2-fluoro-4-methoxyphenyl)-4-(2-fluorobenzyl)-6-methoxy-1,2-dihydronaphthalene | 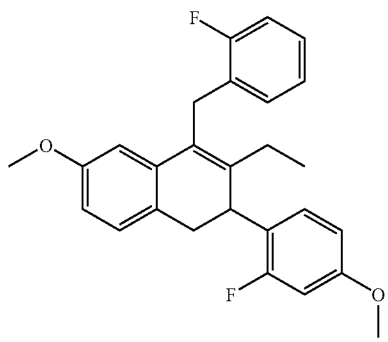 | 87% | ¹H NMR (CDCl$_3$): δ 0.88 (t, 3H), 1.89 (m, 1H), 2.41 (m, 1H), 2.81 (m, 1H), 3.21 (m, 1H), 3.67 (s, 3H), 3.74 (s, 3H), 3.98 (AB, J = 16 Hz, J = 46 Hz, 2H). |
| 7p | 2-(2-fluoro-4-methoxyphenyl)-4-(2-fluorobenzyl)-6-methoxy-3-methyl-1,2-dihydronaphthalene | 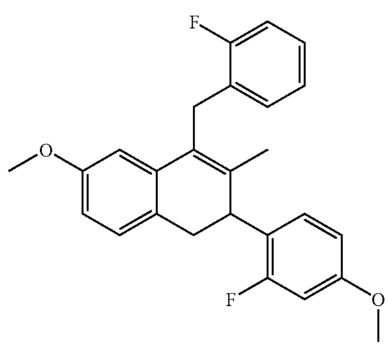 | 87% | ¹H NMR (CDCl$_3$): δ 1.84 (s, 3H), 2.82 (dd, J1 = 15 Hz, J2 = 4 Hz, 1H), 3.27 (dd, J1 = 15 Hz, J2 = 8 Hz, 1H), 3.45 (dd, J1 = 8 Hz, J2 = 4 Hz, 1H), 3.67 (s, 3H), 3.74 (s, 3H), 3.91 (AB, J = 16 Hz, J = 46 Hz, 2H), 6.57 (dd, J1 = 9 Hz, J2 = 2 Hz, 1H), 6.72 (s, 1H), 6.87 (d, J = 9 Hz, 1H), 6.88 (AB, J1 = 105 Hz, J2 = 9 Hz, 4H), 6.95 (dd, J1,2 = 9 Hz, 2H), 7.19 (m, 2H). |
| 7q | 3-ethyl-2-(3-fluoro-4-methoxyphenyl)-4-(2-fluorobenzyl)-6-methoxy-1,2-dihydronaphthalene | 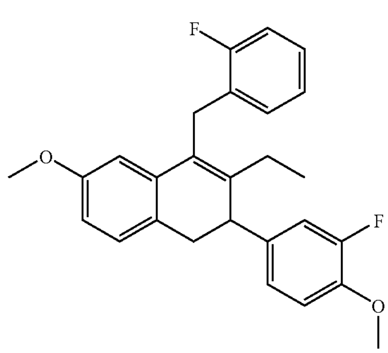 | 69% | ¹H NMR (CDCl$_3$): δ 1.04 (t, J = 8 Hz, 3H), 1.94 (m, 1H), 2.42 (m, 1H), 2.83 (dd, J1 = 3 Hz, J2 = 15 Hz, 1H), 3.27 (dd, J1 = 15 Hz, J2 = 8 Hz, 1H), 3.57 (dd, J1 = 3 Hz, J2 = 8 Hz, 1H), 3.67 (s, 3H), 3.82 (s, 3H), 3.97 (AB, J = 17 Hz, J = 44 Hz, 2H), 6.57 (dd, J1 = 14 Hz, J2 = 3 Hz, 1H), 6.72 (d, J = 3 Hz, 1H). |

TABLE 1-continued

Compounds prepared according to General Procedure I

| Compound | Name | Structure | Yield | $^1$H NMR |
|---|---|---|---|---|
| 7r | 4-(2-fluorobenzyl)-6-methoxy-2-(4-methoxy-3-methylphenyl)-3-methyl-1,2-dihydroaphthalene | 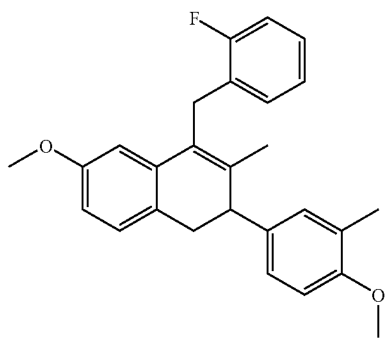 | 41% | $^1$H NMR (CDCl$_3$): δ 1.84 (s, 3H), 2.14 (s, 3H), 2.83 (dd, J1 = 15 Hz, J2 = 4 Hz, 1H), 3.28 (dd, J1 = 15 Hz, J2 = 8 Hz, 1H), 3.44 (dd, J1 = 8 Hz, J2 = 4 Hz, 1H), 3.69 (s, 3H), 3.77 (s, 3H), 3.95 (AB, J = 16 Hz, J = 36 Hz, 2H), 6.57 (dd, J1 = 9 Hz, J2 = 3 Hz, 1 H), 6.64 (d, J = 9 Hz, 1H), 6.73 (d, J = 3 Hz, 1H). |
| 7s | 5-fluoro-4-(2-fluorobenzyl)-6-methoxy-2-(4-methoxyphenyl)-3-methyl-1,2-dihydro-naphthalene | 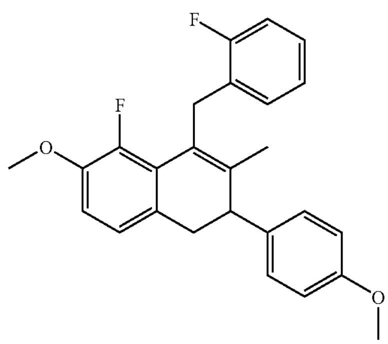 | 77% | $^1$H NMR (CDCl$_3$): δ 1.89 (s, 3H), 2.77 (dd, J1 = 15 Hz, J2 = 4 Hz, 1H), 3.27 (dd, J1 = 15 Hz, J2 = 8 Hz, 1H), 3.45 (dd, J1 = 8 Hz, J2 = 4 Hz, 1H), 3.72 (s, 3H), 3.75 (s, 3H), 3.95 (q, J = 17 Hz, 2H), 6.68 (d, J = 11 Hz, 1H), 6.88 (AB, J1 = 104 Hz, J2 = 9 Hz, 4H), 6.77-7.20 (m, 5H) |
| 7v | 3-ethyl-6-methoxy-2-(4-methoxyphenyl)-4-(2-methylbenzyl)-1,2-dihydronaphthalene | 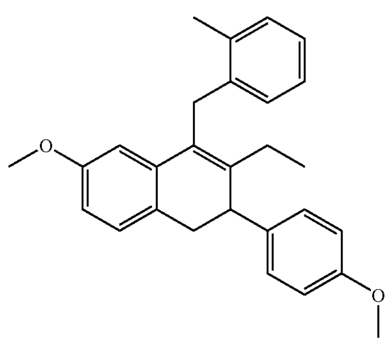 | 100% | $^1$H NMR (CDCl$_3$): δ 1.03 (t, J = 8 Hz, 3H), 1.88 (m, 1H), 2.31 (m, 1H), 2.45 (s, 3H), 2.86 (dd, J1 = 2 Hz, J2 = 15 Hz, 1H), 3.31 (dd, J1 = 15 Hz, J2 = 8 Hz, 1H), 3.59 (dd, J1 = 2 Hz, J2 = 8 Hz, 1H), 3.63 (s, 3H), 3.74 (s, 3H), 3.84 (AB, J = 17 Hz, J = 44 Hz, 2H), 6.87 (AB, J1 = 9 Hz, J2 = 124 Hz, 4H), 6.88 (d, J = 9 Hz, 1H). |
| 7w | 3-ethyl-4-(4-fluorobenzyl)-6-methoxy-2-(4-methoxyphenyl)-1,2-dihydronaphthalene | 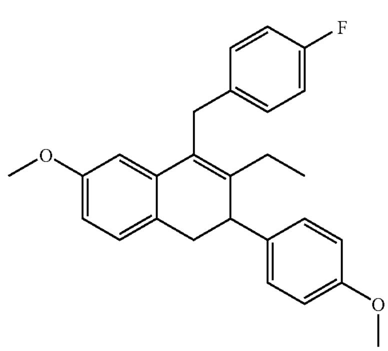 | 105% (‡) | $^1$H NMR (CDCl$_3$): δ 1.05 (t, J = 7 Hz, 3H), 1.93 (m, 1H), 2.40 (m, 1H), 2.84 (dd, J1 = 2 Hz, J2 = 15 Hz, 1H), 3.27 (dd, J1 = 15 Hz, J2 = 8 Hz, 1H), 3.57 (dd, J1 = 2 Hz, J2 = 8 Hz, 1H), 3.66 (s, 3H), 3.74 (s, 3H), 3.93 (AB, J = 17 Hz, J = 57 Hz, 2H), 6.56 (dd, J1 = 8 Hz, J2 = 3 Hz, 1H), 6.71 (d, J = 3 Hz, 1H), 6.83 (AB, J1 = 9 Hz, J2 = 110 Hz, 4H). |

TABLE 1-continued

Compounds prepared according to General Procedure I

| Compound | Name | Structure | Yield | ¹H NMR |
|---|---|---|---|---|
| 7y | 4-(2,6-difluorobenzyl)-5-fluoro-6-methoxy-2-(4-methoxyphenyl)-3-methyl-1,2-dihydronaphthalene | 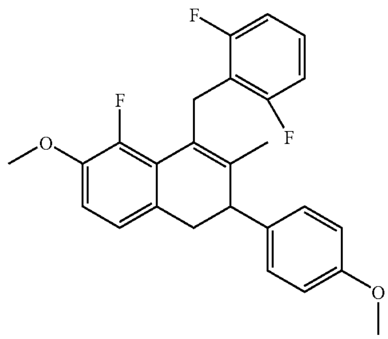 | 96% | ¹H NMR (CDCl$_3$): δ 1.89 (s, 3H), 2.66 (dd, J1 = 15 Hz, J2 = 4 Hz, 1H), 3.16 (dd, J1 = 15 Hz, J2 = 8 Hz, 1H), 3.42 (dd, J1 = 8 Hz, J2 = 4 Hz, 1H), 3.74 (s, 3H), 3.84 (s, 3H), 4.03 (q, J = 18 Hz, 2H), 6.62 (d, J = 11 Hz, 1H), 6.84 (AB, J1 = 91 Hz, J2 = 9 Hz, 4H), 6.78-7.19 (m, 5H) |

Notes:
(§) starting from compound 20;
(‡) crude yield;
compound used as such in next step.

Example 11

Procedure for the preparation of 1-(2-fluorobenzyl)-7-methoxy-3-(4-methoxy-phenyl)-2-methyl-1,2,3,4-tetrahydronaphthalene (compound 8a)
General Procedure J (See Scheme 2)

Palladium (10% on activated carbon 4.85 g, 4.09 mmol) was suspended in ethyl acetate (200 ml) and H$_2$ gas was led through the suspension for 30 min. Compound 7a (15.90 g, 40.9 mmol) and 2,6-di-tert-butyl-4-methylpyridine (20.98 g, 110 mmol) was dissolved in 100 ml ethyl acetate and was added in 6 portions over a period of 2 h. The reaction mixture was stirred for 16 h under continuous bubbling of H$_2$. Nitrogen was led through the reaction mixture for 30 min. The reaction mixture was filtered over decalite. The filtrate was concentrated to give a colorless oil. NMR showed 72% all cis product, 21% trans products and 7% of the naphthalene product. The crude oil was purified by silica gel chromatography (heptane/ethyl acetate 9/1) to give the compound 8a as a colorless oil (15.04 g, 52%). ¹H NMR (CDCl$_3$): see Table 2.

According to General Procedure J the compounds in Table 2 were synthesized:

TABLE 2

Compounds prepared according to General Procedure J

| Compound | Name | Structure | Yield | ¹H NMR |
|---|---|---|---|---|
| 8a | 1-(2-fluorobenzyl)-7-methoxy-3-(4-methoxyphenyl)-2-methyl-1,2,3,4-tetrahydronaphthalene | 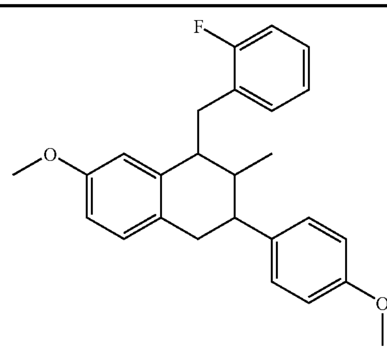 | 52% | ¹H NMR (CDCl$_3$): δ 0.66 (d, J = 7 Hz, 3H), 1.87 (m, 1H), 3.29 (dd, J1" = 15 Hz, J2" = 7 Hz, 1H), 3.60 (dd, J1 = 5 Hz, J2 = 7 Hz, 1H), 3.75 (s, 3H), 3.82 (s, 3H), 6.73 (dd, J1 = 9 Hz, J2 = 2 Hz, 1H), 6.86 (AB, J1 = 84 Hz, J2 = 18 Hz, 4H), 6.93 (d, J = 9 Hz, 1H) |
| 8c | 1-(2-fluorobenzyl)-7-methoxy-3-(4-methoxyphenyl)-2-propyl-1,2,3,4-tetrahydronaphthalene | 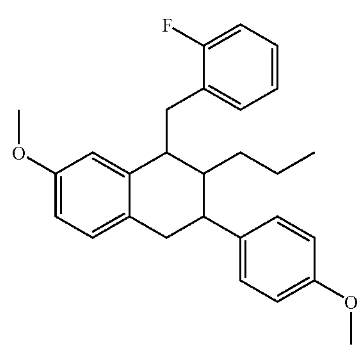 | 68% | ¹H NMR (CDCl$_3$): δ 0.65 (t, J = 7 Hz, 3H), 0.75 (t, J = 7 Hz, 3H), 0.82 (t, J = 7 Hz, 3H), 2.10 (m, 1H), 2.68 (m, 1H), 2.83 (m, 1H), 3.28 (m, 1H), 3.47 (m, 1H), 7.01 (AB, J1 = 9 Hz, J2 = 116 Hz, 4H). |

TABLE 2-continued

Compounds prepared according to General Procedure J

| Compound | Name | Structure | Yield | $^1$H NMR |
|---|---|---|---|---|
| 8d | 1-(benzyl)-7-methoxy-3-(4-methoxyphenyl)-2-methyl-1,2,3,4-tetrahydronaphthalene | 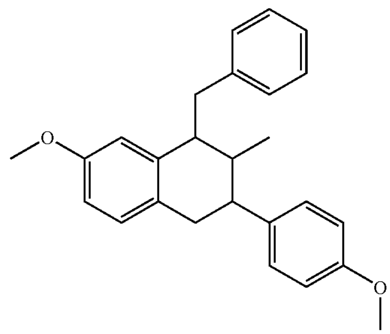 | 100% | $^1$H NMR (CDCl$_3$): δ 0.63 (d, J = 6 Hz, 3H), 2.01 (m, 1H), 2.71 (m, 1H), 2.89 (m, 1H), 3.16 (m, 2H), 3.52 (m, 2H), 3.76 (s, 3H), 3.78 (s, 3H). |
| 8e | 1-(benzyl)-7-methoxy-3-(4-methoxyphenyl)-2-ethyl-1,2,3,4-tetrahydronaphthalene | 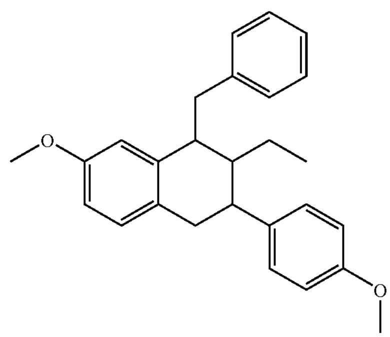 | 60% | $^1$H NMR (CDCl$_3$): δ 0.58 (t, J = 8 Hz, 3H), 1.33 (m, 2H), 2.04 (m, 1H), 2.81 (dd, J1 = 8 Hz, J2 = 14 Hz, 2H), 3.26 (m, 2H), 3.46 (m, 1H), 3.63 (s, 3H), 3.77 (s, 3H). |
| 8f | 1-(3-fluorobenzyl)-7-methoxy-3-(4-methoxyphenyl)-2-methyl-1,2,3,4-tetrahydronaphthalene | 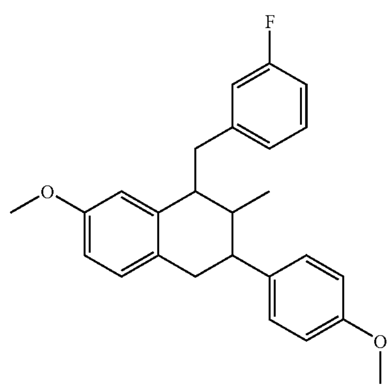 | 54% | $^1$H NMR (CDCl$_3$): δ 0.62 (d, J = 6 Hz, 3H), 1.97 (m, 1H), 2.71 (dd, J1 = 11 Hz, J2 = 16 Hz, 1H), 2.89 (d, J1 = 14 Hz, 1H), 3.15 (m, 2H), 3.45 (m, 2H), 3.76 (s, 3H), 3.77 (s, 3H), 6.77 (dd, J1 = 13 Hz, J2 = 3 Hz, 1H), 7.00 (AB, J1 = 9 Hz, J2 = 116 Hz, 4H).. |
| 8g | 1-(4-fluorobenzyl)-7-methoxy-3-(4-methoxyphenyl)-2-methyl-1,2,3,4-tetrahydronaphthalene | 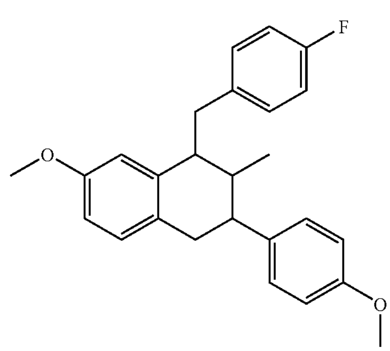 | 55% | $^1$H NMR (CDCl$_3$): δ 0.62 (d, J = 6 Hz, 3H), 1.96 (m, 1H), 2.67 (dd, J1 = 11 Hz, J2 = 16 Hz, 1H), 2.89 (dd, J1 = 14 Hz, J2 = 3 Hz, 1H), 3.15 (m, 2H), 3.47 (m, 2H), 3.77 (s, 6H), 6.57 (dd, J1 = 13 Hz, J2 = 3 Hz, 1H), 6.84 (d, J = 9 Hz, 2H). |

TABLE 2-continued

Compounds prepared according to General Procedure J

| Compound | Name | Structure | Yield | ¹H NMR |
|---|---|---|---|---|
| 8h | 1-(2,5-difluorobenzyl)-7-methoxy-3-(4-methoxyphenyl)-2-methyl-1,2,3,4-tetrahydronaphthalene | 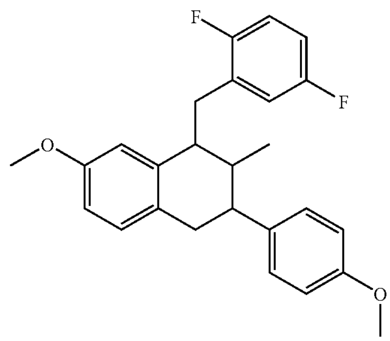 | 100% | ¹H NMR (CDCl$_3$): δ 0.65 (d, J = 7 Hz, 3H), 1.97 (m, 1H), 2.76 (dd, J1 = 9 Hz, J2 = 14 Hz, 1H), 2.89 (m, 1H), 3.16 (m, 2H), 3.45 (m, 2H), 3.78 (s, 3H), 3.79 (s, 3H), 6.60-7.35 (m, 10H). |
| 8i | 1-(2,6-difluorobenzyl)-7-methoxy-3-(4-methoxyphenyl)-2-methyl-1,2,3,4-tetrahydronaphthalene | 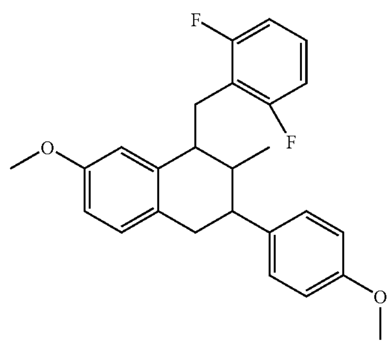 | 81% | ¹H NMR (CDCl$_3$): δ 0.68 (d, J = 6 Hz, 3H), 1.94 (m, 1H), 2.82 (m, 2H), 3.16 (m, 2H), 3.44 (m, 1H), 3.62 (m, 1H), 3.78 (s, 3H), 3.82 (s, 3H), 6.75-7.20 (m, 10H). |
| 8j | 2-((2-methyl-7-methoxy-3-(4-methoxyphenyl)-1,2,3,4-tetrahydronaphthalene-1-yl)methyl)benzonitrile | 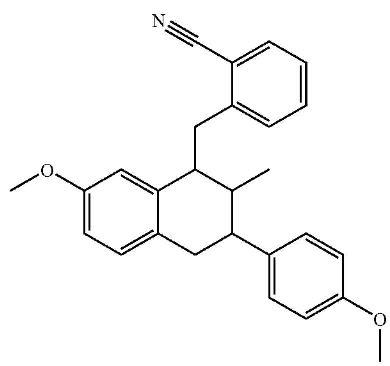 | 21% | ¹H NMR (CDCl$_3$): δ 0.71 (d, J = 7 Hz, 3H), 1.94 (m, 1H), 2.89 (m, 1H), 3.01 (dd, J1 = 12 Hz, J2 = 16 Hz, 1H), 3.18 (m, 2H), 3.69 (m, 2H), 3.78 (s, 3H), 3.80 (s, 3H), 6.78 (dd, J1 = 2 Hz, J2 = 8 Hz, 1H), 7.00 (d, J = 2 Hz, 1H), 7.01 (AB, J1 = 9 Hz, J2 = 120 Hz, 4H), 7.31-7.70 (m, 4H). |
| 8k | 2-((2-ethyl-7-methoxy-3-(4-methoxyphenyl)-1,2,3,4-tetrahydronaphthalene-1-yl)methyl)benzonitrile | 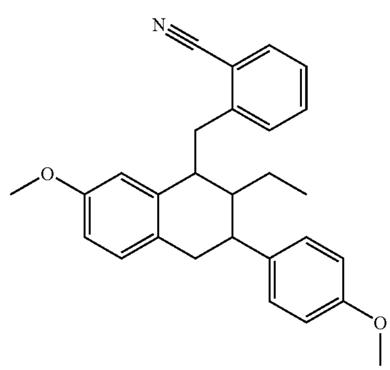 | 4% | (‡) |

TABLE 2-continued

Compounds prepared according to General Procedure J

| Compound | Name | Structure | Yield | ¹H NMR |
|---|---|---|---|---|
| 8l | 1-(2-chlorobenzyl)-7-methoxy-3-(4-methoxyphenyl)-2-methyl-1,2,3,4-tetrahydronaphthalene | 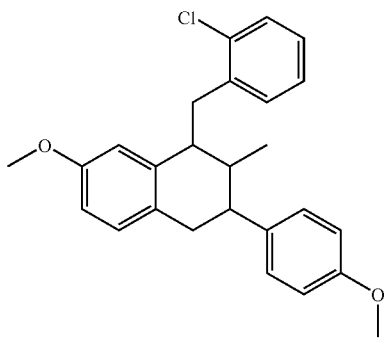 | 100% | ¹H NMR (CDCl$_3$): δ 0.71 (d, J = 7 Hz, 3H), 1.99 (m, 1H), 2.86 (m, 1H), 3.15 (m, 1H), 3.18 (m, 2H), 3.76 (s, 3H), 3.78 (s, 3H). |
| 8m | 7-methoxy-1-(4-methoxyphenyl)-3-(4-methoxyphenyl)-2-methyl-1,2,3,4-tetrahydronaphthalene | 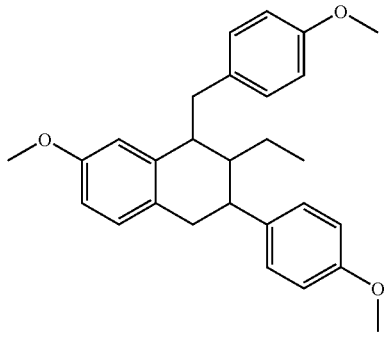 | 73% | ¹H NMR (CDCl$_3$): δ 0.55 (t, J = 8 Hz, 3H), 1.30 (m, 2H), 2.03 (m, 1H. |
| 8n | 6-(4-hydroxyphenyl)-8-(2-methoxybenzyl)-7-methyl-5,6,7,8-tetrahydronaphthalene-2-ol | 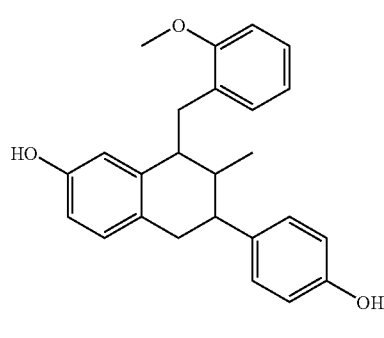 | 9% | ¹H NMR (CDCl$_3$): δ 0.66 (d, J = 7 Hz, 3H), 1.94 (m, 1H), 2.71 (dd, J1 = 10 Hz, J2 = 14 Hz, 1H), 2.85 (m, 1H), 3.12 (m, 2H), 3.48 (m, 2H), 3.57 (m, 1H), 3.84 (s, 3H), 6.68 (dd, J1 = 8 Hz, J2 = 2 Hz, 1H), 6.90 (m, 2H), 6.92 (AB, J1 = 9 Hz, J2 = 128 Hz, 4H), 7.00 (d, J = 2 Hz, 1H), 7.04 (d, J = 8 Hz, 1H), 7.24 (m, 2H). |
| 8o | 2-ethyl-3-(2-fluoro-4-methoxyphenyl)-1-(2-fluorobenzyl)-7-methoxy-1,2,3,4-tetrahydronaphthalene | 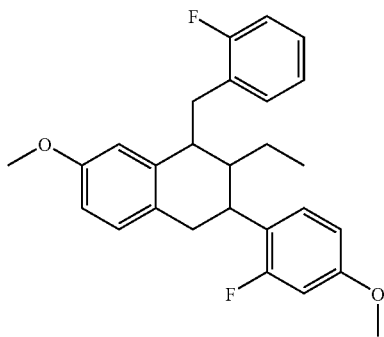 | 60% | ¹H NMR (CDCl$_3$): δ 0.64 (t, J = 7 Hz, 3H), 2.04 (m, 1H), 6.50-7.30 (m, 10H). |

TABLE 2-continued

Compounds prepared according to General Procedure J

| Compound | Name | Structure | Yield | ¹H NMR |
|---|---|---|---|---|
| 8p | 3-(2-fluoro-4-methoxyphenyl)-1-(2-fluorobenzyl)-7-methoxy-2-methyl-1,2,3,4-tetrahydronaphthalene | 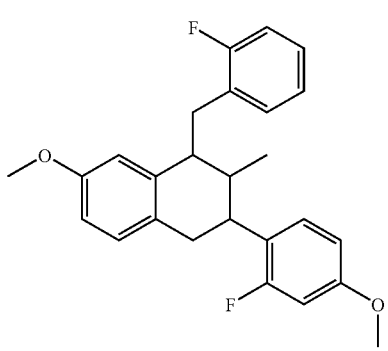 | 49% | ¹H NMR (CDCl$_3$): δ 0.64 (d, J = 7 Hz, 3H), 2.00 (m, 1H), 6.50-7.36 (m, 10H). |
| 8q | 2-ethyl-3-(3-fluoro-4-methoxyphenyl)-1-(2-fluorobenzyl)-7-methoxy-1,2,3,4-tetrahydronaphthalene | 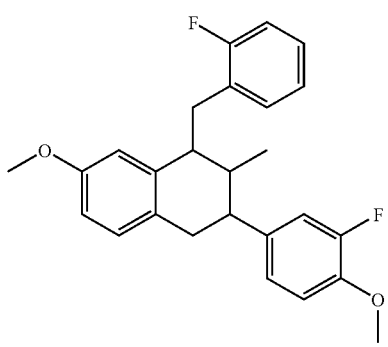 | 65% | ¹H NMR (CDCl$_3$): δ 0.60 (t, J = 7 Hz, 3H), 2.03 (m, 1H), 2.83 (m, 1H), 3.16 (m, 2H), 3.45 (m, 2H), 3.67 (s, 3H), 3.88 (s, 3H), 6.60-7.25 (m, 10H). |
| 8r | 1-(2-fluorobenzyl)-7-methoxy-3-(4-methoxy-3-methylphenyl)-2-methyl-1,2,3,4-tetrahydronaphthalene | 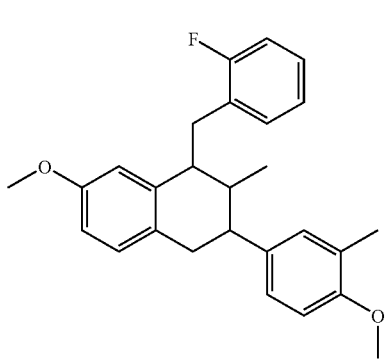 | 55% | ¹H NMR (CDCl$_3$): δ 0.68 (d, J = 7 Hz, 3H), 1.94 (m, 1H), 2.20 (s, 3H), 3.80 (m, 6H). |
| 8s | 8-fluoro-1-(2-fluorobenzyl)-1,2,3,4-tetrahydro-7-methoxy-3-(4-methoxyphenyl)-2-methylnaphthalene | 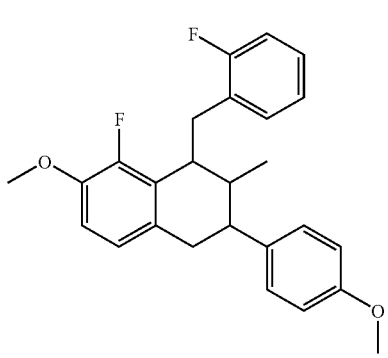 | 94% | ¹H NMR (CDCl$_3$): δ 0.66 (d, J = 7 Hz, 3H), 2.28 (m, 1H), 2.55 (dd, J1 = J2 = 13 Hz, 1H), 2.75-3.88 (m, 11H), 6.73-7.35 (m, 10H) |

TABLE 2-continued

Compounds prepared according to General Procedure J

| Compound | Name | Structure | Yield | ¹H NMR |
|---|---|---|---|---|
| 8v | 2-ethyl-7-methoxy-3-(4-methoxyphenyl)-1-(2-methylbenzyl)-1,2,3,4-tetrahydronaphthalene | 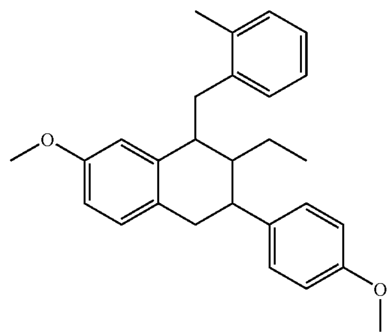 | 11% | ¹H NMR (CDCl$_3$): δ 0.71 (t, J = 8 Hz, 3H), 1.45 (m, 2H), 2.32 (m, 1H), 2.81 (ddd, J1 = 8 Hz, J2 = 14 Hz, J3 = 77 Hz, 2H), 3.11 (m, 1H), 3.28 (m, 2H), 3.28 (m, 1H), 3.55 (s, 3H), 3.78 (s, 3H), 6.41 (d, J = 3 Hz, 1H), 6.73 (dd, J1 = 3 Hz, J2 = 9 Hz, 1H), 7.03 (AB, J1 = 8 Hz, J2 = 152 Hz, 4H), 7.10-7.17 (m, 5H). |
| 8w | 2-ethyl-1-(4-fluorobenzyl)-7-methoxy-3-(4-methoxyphenyl)-2-propyl-1,2,3,4-tetrahydronaphthalene | 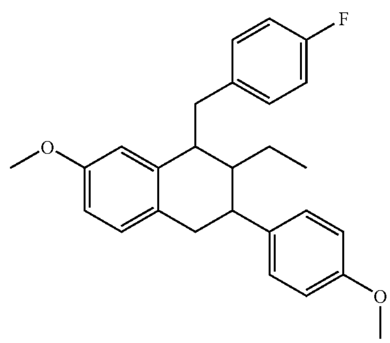 | 57% | ¹H NMR (CDCl$_3$): δ 0.57 (t, J = 6 Hz, 3H), 1.32 (m, 2H), 2.02 (m, 1H), 2.75 (m, 2H), 3.08 (m, 2H), 3.26 (m, 1H), 3.39 (m, 1H), 6.64 (m, 11H). |
| 8y | 1-(2,6-difluorobenzyl)-8-fluoro-1,2,3,4-tetrahydro-7-methoxy-3-(4-methoxyphenyl)-2-methyl-naphthalene | 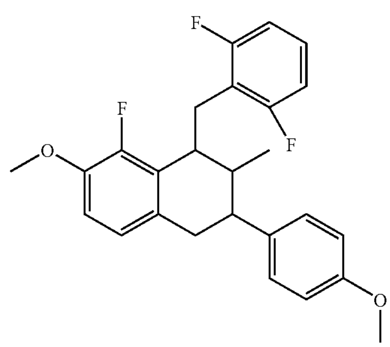 | 82% | ¹H NMR (CDCl$_3$): δ 0.66 (d, J = 7 Hz, 3H), 2.29 (m, 1H), 2.73 (dd, J1 = J2 = 11 Hz, 1H), 2.79-3.18 (m, 5H), 3.78 (s, 3H), 3.88 (s, 3H), 6.75-7.23 (m, 10H) |
| 10b (ξ) | 4-(-6-acetoxy-3-ethyl-4-(2-fluorobenzyl)-1,2,3,4-tetrahydronaphthalen-2-yl)phenyl acetate | 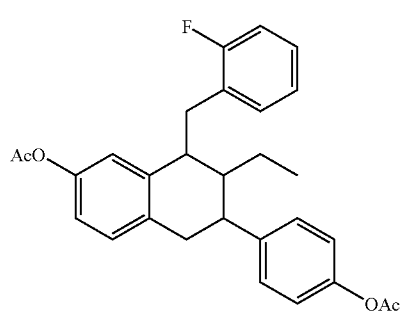 | 24% | ¹H NMR (CDCl$_3$): δ 0.48 (t, J = 7 Hz, 3H), 1.32 (m, 2H), 2.00 (m, 1H), 2.27 (s, 3H), 2.28 (s, 3H), 2.83 (dd, J1 = 14 Hz, J2 = 9 Hz, 1H), 3.09-3.39 (m, 4H), 3.52 (m, 1H), 6.86-7.27 (m, 11H) |

Notes: ξ) prepared starting from compound 24; (‡) crude product; compound used as such in next step.

Example 12

Procedure for the preparation of 8-(2-fluorobenzyl)-6-(4-hydroxyphenyl)-7-methyl-5,6,7,8-tetrahydronaphthalen-2-ol (compound 9a)
General Procedure K (See Scheme 2)

Compound 8a (11.40 g, 29.20 mmol) was dissolved in dichloromethane (250 ml) to obtain a clear colorless solution. This solution was cooled to 0° C. and then boron tribromide (25.3 ml, 263 mmol) was added carefully to give a brown solution. The mixture was stirred at room temperature for 2 h and then poured into ice water (250 ml) and extracted with dichloromethane (2×200 ml). The organic phases were combined, washed with a saturated sodium bicarbonate solution (250 ml) and water (250 ml), dried with sodium sulfate and concentrated. The crude product was purified by column chromatography (toluene/ethyl acetate 95:5) to give compound 9a as a yellow oil (7.80 g, 73% yield). $^1$H NMR (CDCl$_3$): see Table 3.

According to General Procedure K (unless stated otherwise) the compounds in Table 3 were synthesized:

TABLE 3

Compounds synthesized according to General Procedure K.

| Compound | Name | Structure | Yield | purity (%) | Rf (min) | $^1$H NMR |
|---|---|---|---|---|---|---|
| 9a | 8-(2-fluorobenzyl)-6-(4-hydroxyphenyl)-7-methyl-5,6,7,8-tetrahydronaphthalen-2-ol | 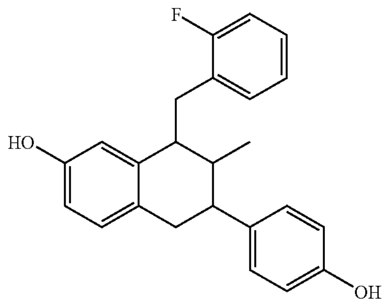 | 73% | 100 | 9.74 (¤ a) | $^1$H NMR: δ 0.63 (d, J = 7 Hz, 3H), 1.92 (m, 1H), 2.74 (dd, J1 = 14 Hz, J2 = 10 Hz, 1H), 2.85 (d, J = 12 Hz, 1H), 3.12 (m, 2H), 3.51 (m, 2H), 5.06 (s, OH), 5.07 (s, OH), 6.68 (dd, J1 = 9 Hz, J2 = 3 Hz, 1H), 6.93 (AB, J1 = 126 Hz, J2 = 9 Hz, 4H), 6.96 (d, J = 3 Hz, 1H), 7.07 (m, 3H), 7.20 (m, 1H), 7,28 (t, 1H) |
| 9b | 8-(2-fluorobenzyl)-6-(4-hydroxyphenyl)-7-ethyl-5,6,7,8-tetrahydronaphthalen-2-ol | 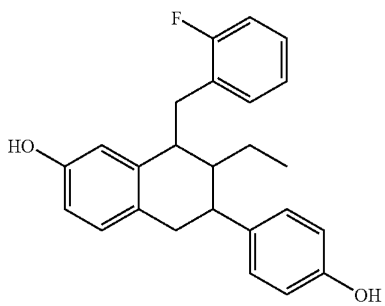 | | 99.6 | 15.38 (♣ a) | $^1$H NMR (DMSO): δ 0.32 (t, J = 8 Hz, 3H), 1.14 (m, 2H), 1.77 (m, 1H), 2.75 (dd, J1 = 9 Hz, J2 = 16 Hz, 1H), 2.86 (d, J = 10 Hz, 1H), 3.10-3.27 (m, 3H), 3.44 (m, 1H), 6.57 (dd, J1 = 9 Hz, J2 = 2 Hz, 1H), 6.63-7.33 (9H), 7.39 (m, 1H) |
| 9c | 8-(2-fluorobenzyl)-6-(4-hydroxyphenyl)-7-propyl-5,6,7,8-tetrahydronaphthalen-2-ol | 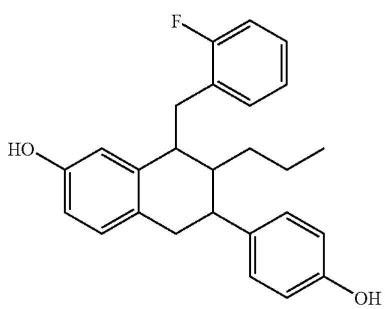 | 31% | 98.6 | 6.01 ($ a) | $^1$H NMR (CDCl$_3$): δ 0.62 (t, J = 6 Hz, 3H), 0.76 (m, 1H), 0.88 (m, 1H), 1.22 (m, 2H), 2.03 (m, 1H), 2.81 (dd, J1 = 8 Hz, J2 = 14 Hz, 1H), 3.01 (m, 1H), 3.20 (m, 3H), 3.44 (m, 1H), 6.64 (d, J = 3, 1H), 6.68 (dd, J1 = 7 Hz, J2 = 3 Hz, 1H), 6.91 (AB, J1 = 9 Hz, J2 = 141 Hz, 4H). |
| 9d | 8-benzyl-6-(4-hydroxyphenyl)-7-methyl-5,6,7,8-tetrahydronaphthalen-2-ol | 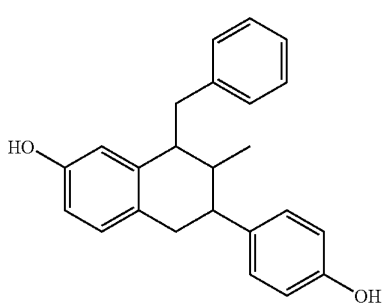 | (ξ) | 99.1 | 14.54 (♪ e) | $^1$H NMR (CDCl$_3$): δ 0.62 (d, J = 7 Hz, 3H), 1.97 (m, 1H), 2.68 (dd, J1 = 11 Hz, J2 = 15 Hz, 1H), 2.87 (m, 1H), 3.13 (m, 2H), 3.50 (m, 2H), 6.68 (dd, J1 = 8 Hz, J2 = 3 Hz, 1H), 6.91 (AB, J1 = 9 Hz, J2 = 129 Hz, 4H), 7.06 (d, J = 8 Hz, 1H), 7.21-7.35 (m, 5H). |

TABLE 3-continued

Compounds synthesized according to General Procedure K.

| Compound | Name | Structure | Yield | purity (%) | Rf (min) | ¹H NMR |
|---|---|---|---|---|---|---|
| 9e | 8-benzyl-7-ethyl-6-(4-hydroxyphenyl)-5,6,7,8-tetrahydronaphthalen-2-ol | 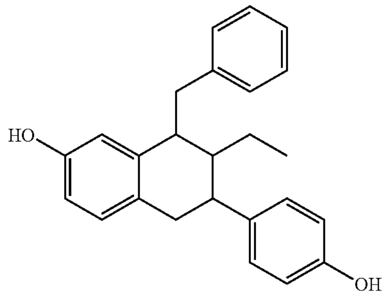 | 18% | 97.3 | 17.70 (♪ d) | ¹H NMR (CDCl$_3$): δ 0.53 (t, J = 8 Hz, 3H), 1.29 (m, 2H), 2.00 (m, 1H), 2.78 (dd, J1 = 8 Hz, J2 = 15 Hz, 1H), 3.04 (m, 1H), 3.21 (m, 3H), 3.44 (m, 1H), 6.66 (m, 2H), 6.92 (AB, J1 = 9 Hz, J2 = 149 Hz, 4H), 7.07 (d, J = 8 Hz, 1H), 7.22-7.35 (m, 5H). |
| 9f | 8-(3-fluorobenzyl)-6-(4-hydroxyphenyl)-7-methyl-5,6,7,8-tetrahydronaphthalen-2-ol | 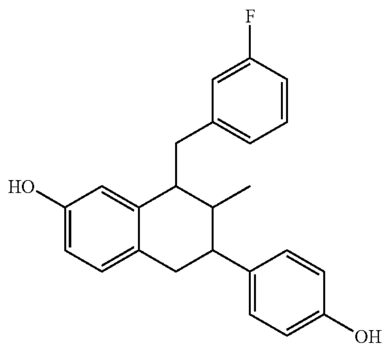 | 94% | 85 (*) | | ¹H NMR (CDCl$_3$): δ 0.61 (d, J = 7 Hz, 3H), 1.96 (m, 1H), 2.67 (dd, J1 = 11 Hz, J2 = 15 Hz, 1H), 2.87 (m, 1H), 3.12 (m, 2H), 3.47 (m, 2H), 6.69 (dd, J1 = 7 Hz, J2 = 3 Hz, 1H), 6.93 (AB, J1 = 9 Hz, J2 = 122 Hz, 4H). |
| 9g | 8-(4-fluorobenzyl)-6-(4-hydroxyphenyl)-7-methyl-5,6,7,8-tetrahydronaphthalen-2-ol | 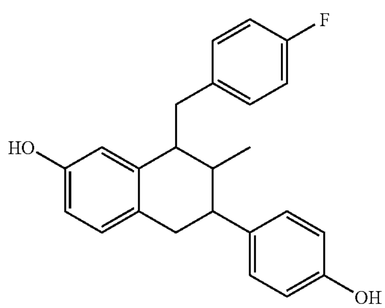 | 100% | 95 (*) | | ¹H NMR (CDCl$_3$): δ 0.60 (d, J = 7 Hz, 3H), 1.93 (m, 1H), 2.64 (m, 1H), 2.86 (m, 1H), 3.11 (m, 2H), 3.44 (m, 2H), 6.68 (dd, J1 = 7 Hz, J2 = 3 Hz, 1H), 6.91 (AB, J1 = 9 Hz, J2 = 120 Hz, 4H), 6.92 (d, J = 3 Hz, 1H). |
| 9h | 8-(2,5-fluorobenzyl)-6-(4-hydroxyphenyl)-7-methyl-5,6,7,8-tetrahydronaphthalen-2-ol | 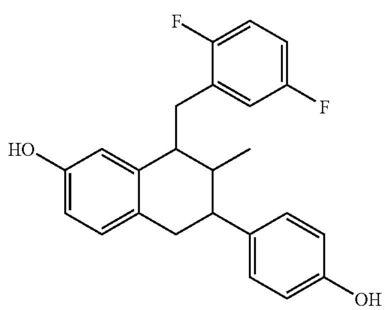 | 96% | 95.9 | 8.34 (♪ b) | ¹H NMR (CDCl$_3$): δ 0.64 (d, J = 7 Hz, 3H), 1.92 (m, 1H), 2.72 (dd, J1 = 9 Hz, J2 = 14 Hz, 1H), 2.86 (m, 1H), 3.11 (m, 2H), 3.44 (m, 2H), 6.69 (dd, J1 = 7 Hz, J2 = 3 Hz, 1H), 6.91 (AB, J1 = 9 Hz, J2 = 122 Hz, 4H), 6.92 (d, J = 3 Hz, 1H). |
| 9i | 8-(2,6-difluorobenzyl)-6-(4-hydroxyphenyl)-7-methyl-5,6,7,8-tetrahydronaphthalen-2-ol | 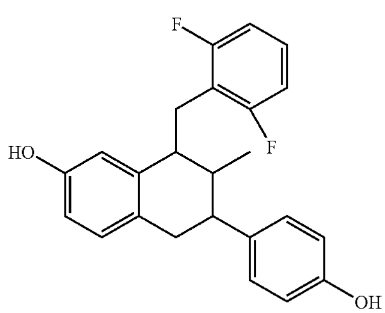 | 40% | 95.1 | 10.00 (♪ a) | ¹H NMR (CDCl$_3$): δ 0.67 (d, J = 7 Hz, 3H), 1.90 (m, 1H), 2.86 (m, 1H), 2.92 (dd, J1 = 11 Hz, J2 = 14 Hz, 1H), 3.14 (m, 2H), 3.40 (dd, J1 = 5 Hz, J2 = 14 Hz, 1H), 3.58 (m, 1H), 6.69 (dd, J1 = 2 Hz, J2 = 8 Hz, 1H), 6.88 (dd, J1 = J2 = 8 Hz, 2H), 6.93 (AB, J1 = 9 Hz, J2 = 130 Hz, 4H), 6.99 (d, J = 2 Hz, 1H), 7.06 (d, J = 8 Hz, 1H). |

TABLE 3-continued

Compounds synthesized according to General Procedure K.

| Compound | Name | Structure | Yield | purity (%) | Rf (min) | $^1$H NMR |
|---|---|---|---|---|---|---|
| 9j | 2-((7-hydroxy-3-(4-hydroxyphenyl)-2-methyl-1,2,3,4-tetrahydronaphthalen-1-yl)methyl)benzonitrile | 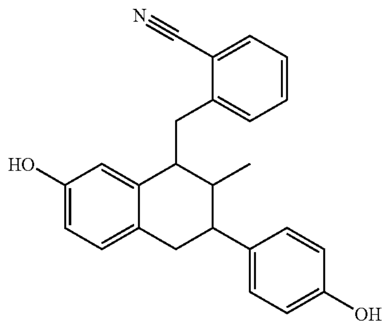 | 90% | 99.2 | 13.94 (♠ a) | $^1$H NMR (CDCl$_3$): δ 0.70 (d, J = 7 Hz, 3H), 1.91 (m, 1H), 2.87 (m, 1H), 2.98 (m, 1H), 3.15 (m, 2H), 3.66 (m, 2H), 3.58 (m, 1H), 6.70 (dd, J1 = 2 Hz, J2 = 8 Hz, 1H), 6.92 (AB, J1 = 9 Hz, J2 = 126 Hz, 4H), 6.96 (d, J = 8 Hz, 1H), 7.35 (dd, J1 = J2 = 7 Hz, 1H), 7.46 (d, J = 7 Hz, 1H), 7.56 (dd, J1 = J2 = 7 Hz, 1H), 7.69 (d, J = 7 Hz, 1H). |
| 9k | 2-((2-ethyl-7-hydroxy-3-(4-hydroxyphenyl)-1,2,3,4-tetrahydronaphthalen-1-yl)methyl)benzonitrile | 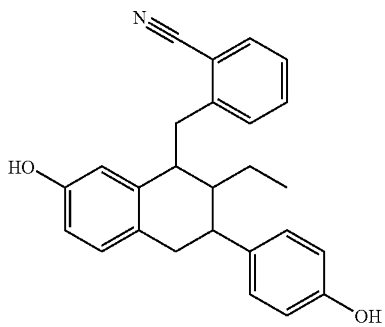 | 35% | 99.8 | 9.24 (♪ a) | $^1$H NMR (CDCl3): δ 0.64 (t, J = 7 Hz, 3H), 1.41 (m, 2H), 2.03 (m, 1H), 2.99 (dd, J1 = 9 Hz, J2 = 15 Hz, 1H), 3.09 (m, 1H), 3.23 (m, 3H), 3.49 (m, 1H), 6.36 (d, J = 3 Hz, 1H), 6.68 (dd, J1 = 3 Hz, J2 = 9 Hz, 1H), 6.94 (AB, J1 = 9 Hz, J2 = 168 Hz, 4H), 7.10 (d, J = 9 Hz, 1H), 7.10-7.26 (m, 4H), 7.28 (d, J = 8 Hz, 1H), 7.23 (dd, J1 = J2 = 8 Hz, 1H), 7.53 (dd, J1 = J2 = 8 Hz, 1H), 7.65 (d, J = 8 Hz, 1H). |
| 9l | 8-(2-chlorobenzyl)-6-(4-hydroxyphenyl)-7-methyl-5,6,7,8-tetrahydronaphthalen-2-ol | 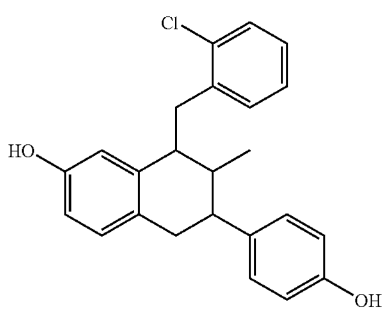 | (ξ) | 99.1 | 15.29 (♪ e) | $^1$H NMR (CDCl3): δ 0.63 (d, J = 7 Hz, 3H), 1.96 (m, 1H), 2.85 (m, 2H), 3.14 (m, 2H), 3.12 (m, 2H), 3.60 (m, 2H), 6.68 (dd, J1 = 8 Hz, J2 = 3 Hz, 1H), 6.95 (AB, J1 = 131 Hz, J2 = 8 Hz, 4H), 6.99 (d, J = 3 Hz, 1H), 7.07 (d, J = 8 Hz, 1H), 7.20 (m, 2H), 7.35 (m, 2H). |
| 9m | 7-ethyl-8-(4-hydroxybenzyl)-6-(4-hydroxyphenyl)-5,6,7,8-tetrahydronaphthalen-2-ol | 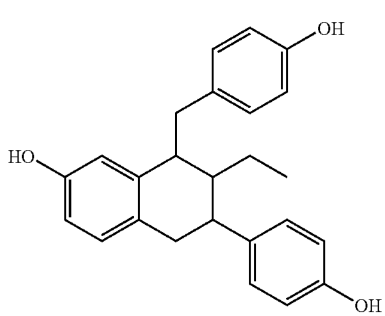 | 9% | 97.2 | 11.90 (# a) | $^1$H NMR (CDCl3): δ 0.53 (t, J = 8 Hz, 3H), 1.41 (m, 2H), 1.99 (m, 1H), 2.70 (m, 1H), 3.05 (m, 1H), 3.21 (m, 3H), 3.35 (m, 1H). |

TABLE 3-continued

Compounds synthesized according to General Procedure K.

| Compound | Name | Structure | Yield | purity (%) | Rf (min) | $^1$H NMR |
|---|---|---|---|---|---|---|
| 9o | 7-ethyl-6-(2-fluoro-4-hydroxyphenyl)-8-(2-fluorobenzyl)-5,6,7,8-tetrahydronaphthalen-2-ol | 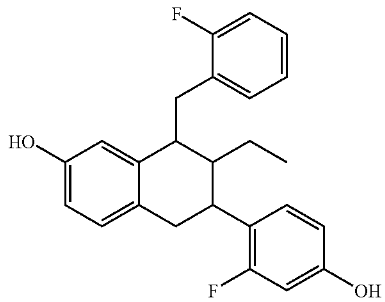 | 16% | 98.2 | 5.30 (♠ a) | $^1$H NMR (CDCl$_3$): δ 0.50 (t, J = 7 Hz, 3H), 1.95 (m, 1H), 2.72 (m, 2H), 3.17 (m, 1H), 3.41 (m, 2H), 3.58 (m, 2H), 6.50 (dd, J1 = 2 Hz, J2 = 11 Hz, 1H), 6.56 (dd, J1 = 2 Hz, J2 = 9 Hz, 1H), 6.68 (dd, J1 = 2 Hz, J2 = 9 Hz, 1H), 6.95 (d, J = 3 Hz, 1H), 7.3 (dt, J1 = 2 Hz, J2 = 6 Hz). |
| 9p | 6-(2-fluoro-4-hydroxyphenyl)-8-(2-fluorobenzyl)-7-methyl-5,6,7,8-tetrahydronaphthalen-2-ol | 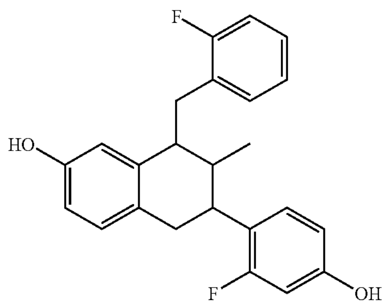 | 35% | 96 | 4.52 (♠ a) | $^1$H NMR (CDCl$_3$): δ 0.62 (d, J = 7 Hz, 3H), 1.95 (m, 1H), 2.72 (m, 2H), 3.17 (m, 1H), 3.41 (m, 2H), 3.58 (m, 2H), 6.50 (dd, J1 = 2 Hz, J2 = 11 Hz, 1H), 6.56 (dd, J1 = 2 Hz, J2 = 9 Hz, 1H), 6.68 (dd, J1 = 2 Hz, J2 = 9 Hz, 1H), 6.95 (d, J = 3 Hz, 1H), 7.3 (dt, J1 = 2 Hz. J2 = 6Hz, 2H). |
| 9q | 7-ethyl-6-(3-fluoro-4-hydroxyphenyl)-8-(2-fluorobenzyl)-5,6,7,8-tetrahydronaphthalen-2-ol | 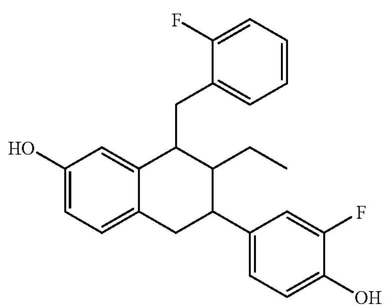 | 7% | 96.1 | 12.30 (♣ c) | $^1$H NMR (CDCl$_3$): δ 0.54 (t, J = 7 Hz, 3H), 1.32 (m, 2H), 1.97 (m, 1H), 2.82 (dd, J1 = 8 Hz, J2 = 14 Hz, 1H), 3.05 (m, 1H), 3.15 (m, 1H), 3.18 (m, 2H), 3.44 (m, 1H), 4.47 (s, OH), 4.94 (s, OH), 6.61 (d, J = 3, 1H), 6.68 (dd, J1 = 7 Hz, J2 = 3 Hz, 1H), 6.87 (m, 8H). |
| 9r | 8-(2-fluorobenzyl)-6-(4-hydroxy-3-methylphenyl)-7-methyl-5,6,7,8-tetrahydronaphthalen-2-ol | 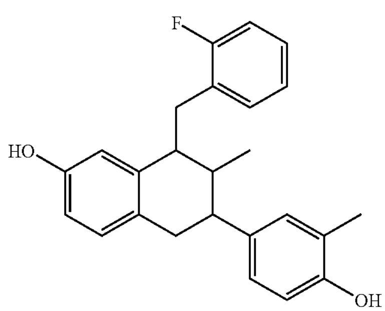 | 8% | 100% | 10.50 (♪) | $^1$H NMR (CDCl$_3$): δ 0.62 (d, J = 8 Hz, 3H), 1.32 (m, 2H), 1.93 (m, 1H), 2.76 (dd, J1 = 14 Hz, J2 = 11 Hz, 1H), 2.84 (dd, J1 = 14 Hz, J2 = 5 Hz, 1H), 3.12 (m, 2H), 3.51 (m, 2H), 4.58 (s, OH), 4.64 (s, OH), 6.68 (dd, J1 = 3 Hz, j2 = 9 Hz, 1H), 6.7 (d, J1 = 9 Hz, 1H), 6.93 (dd, J1 11 Hz, J2 = 2 Hz, 1H), 6.96 (d, J1 = 2 Hz, 2H), 7.7 (m, 3H), 7.21 (m, 1H), 7.3 (dt, J1 = 7 Hz, J2 = 2 Hz, 1H) |
| 9s | 1-fluoro-8-(2-fluorobenzyl)-5,6,7,8-tetrahydro-6-(4-hydroxyphenyl)-7-methylnaphthalen-2-ol | 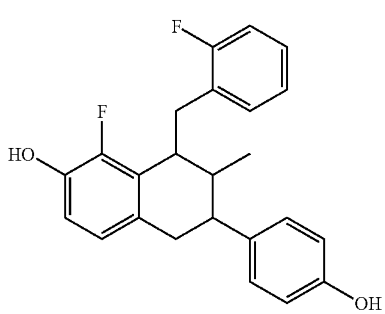 | 12% | 99.3 | 14.79 (♠ b) | $^1$H NMR (CDCl$_3$): δ 0.63 (d, J = 7 Hz, 3H), 1.92 (m, 1H), 2.38-3.52 (m, 7H), 6.91 (AB, J1 = 116 Hz, J2 = 9 Hz, 4H), 6.87 (d, J = 11 Hz, 1H), 7.02-7.33 (m, 5H) |

TABLE 3-continued

Compounds synthesized according to General Procedure K.

| Compound | Name | Structure | Yield | purity (%) | Rf (min) | $^1$H NMR |
|---|---|---|---|---|---|---|
| 9v | 7-ethyl-6-(4-hydroxyphenyl)-8-(2-methylbenzyl)-7-5,6,7,8-tetrahydronaphthalen-2-ol | 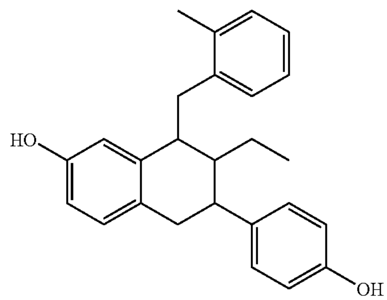 | 50% | 99.7 | 10.79 (♠ a) | $^1$H NMR (DMSO): δ 0.38 (t, J = 7 Hz, 3H), 1.19 (m, 2H), 1.85 (m, 1H), 2.24 (s, 3H), 2.69 (dd, J1 = 9 Hz, J2 = 16 Hz, 1H), 2.88 (m, 1H), 3.14 (m, 3H), 3.41 (m, 1H), 6.55 (dd, J1 = 2 Hz, J2 = 9 Hz, 1H), 6.58 (d, J = 2 Hz, 1H), 6.85 (AB, J1 = 9 Hz, J2 = 151 Hz, 4H), 6.98 (d, J = 9 Hz, 1H), 7.10-7.26 (m, 4H). |
| 9w | 7-ethyl-8-(4-fluorobenzyl)-6-(4-hydroxyphenyl)-5,6,7,8-tetrahydronaphthalen-2-ol | 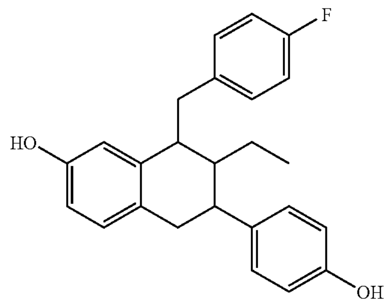 | 5% | 99.4 | 4.64 (♪ a) | $^1$H NMR (DMSO): δ 0.31 (t, J = 7 Hz, 3H), 1.13 (m, 2H), 1.78 (m, 1H), 2.69 (dd, J1 = 9 Hz, J2 = 15 Hz, 1H), 2.85 (m, 1H), 3.14 (m, 2H), 3.27 (dd, J1 = 7 Hz, J2 = 14 Hz, 1H), 3.42 (m, 1H), 6.57 (dd, J1 = 2 Hz, J2 = 9 Hz, 1H), 6.68 (d, J = 2 Hz, 1H), 6.82 (AB, J1 = 9 Hz, J2 = 141 Hz, 4H), 6.98 (d, J = 9 Hz, 1H), 7.10 (dd, J1 = J2 = 8 Hz, 2H), 7.36 (dd, J1 = 5 Hz, J2 = 8 Hz, 2H). |
| 9y | 8-(2,6-difluorobenzyl)-1-fluoro-5,6,7,8-tetrahydro-6-(4-hydroxyphenyl)-7-methylnaphthalen-2-ol | 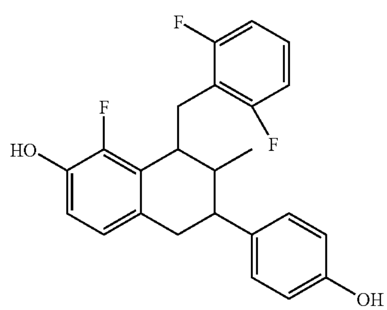 | 5% | 98.2 | 14.89 (♠ b) | $^1$H NMR (CDCl$_3$): δ 0.64 (d, J = 7 Hz, 3H), 1.87 (m, 1H), 2.82 (d, J = 11 Hz, 1H), 2.89 (dd, J1 = 16, J2 = 11 Hz, 1H) 3.04-3.56 (m, 4H), 6.91 (AB, J1 = 118 Hz, J2 = 9 Hz, 4H), 7.09 (d, J = 9 Hz, 1H), 6.84-7.21 (m, 4H) |
| 23 | 7-ethyl-8-(2-fluorobenzyl)-6-(4-hydroxyphenyl)-5,6-dihydronaphthalen-2-ol | 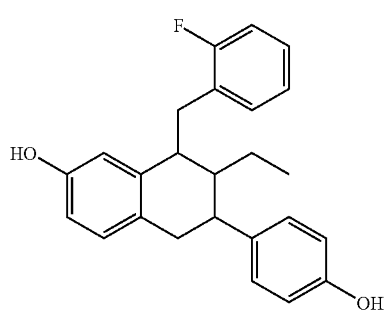 | 99% (‡) | | | $^1$H NMR (CDCl$_3$): δ 1.03 (t, J = 8 Hz, 3H), 1.91 (m, 1H), 2.35 (m, 1H), 2.83 (dd, J1 = 2 Hz, J2 = 15 Hz, 1H), 3.27 (dd, J1 = 15 Hz, J2 = 8 Hz, 1H), 3.56 (dd, J1 = 2 Hz, J2 = 8 Hz, 1H), 3.83 (AB, J = 17 Hz, J = 44 Hz, 2H), 6.51 (dd, J1 = 3 Hz, J2 = 9 Hz, 1H), 6.59 (d, J = 3 Hz, 1H), 6.78 (AB, J1 = 9 Hz, J2 = 130 Hz, 4H), 6.82 (d, J = 9 Hz, 1H), 6.88 (d, J = 9 Hz, 1H). |

Notes: (§) yield not determined; (‡) crude yield; compound used as such in next step; (♪) HPLC on 5µ C18 luna column, gradient acetonitrile in water over 12 min (a) gradient 30 to 90%; (b) gradient 30 to 100%; (c) gradient 20 to 100%; (d) gradient 0 to 90%; (e) gradient 0 to 75% (♠) HPLC on 5µ C18 luna column, 5 min isocratic followed by gradient acetonitrile in water over 12 min (a) gradient 20 to 100%; (b) gradient 30 to 90%; (c) gradient 40 to 100%; ($) HPLC on 5µ C18 luna column, gradient acetonitrile in water over 30 min (a) gradient 60% to 90%; (#) HPLC on 5µ C18 luna column, gradient acetonitrile in water over 30 min (a) gradient 40 to 65%; (□) HPLC on 5µ C18 luna column, 15 min isocratic (50% acetonitril) followed by gradient acetonitrile in water over 10 min (a) gradient 50 to 90%; (*) Purity based on NMR

Example 13

Procedure for the Separation of the Enantiomers of Compounds 9 to Give Single Enantiomers 11 and 12
General Procedure L (See Scheme 5)

The enantiomers of compound 9j were separated on a chiral HPLC column (Chiralpak AS 5μ; 22% isopropanol in heptane). Separation of 90 mg of racemate 9j afforded the single enantiomers 11j (18 mg, chemical purity 95.1%) and 12j (26 mg, chemical purity 97.9%). The enantiomeric excess (e.e.) of the enantiomers was determined on an analytical chiral HPLC column (Chiralpak AS 5μ; 20% isopropanol in heptane): compound 11j: retention time 33.67 min; e.e. 97.8%; compound 12j: retention time 19.67 min; e.e. 100%.

Example 14

Procedure for the Separation of the Enantiomers of Compounds 9 Via Conversion to Bisacetyl Analogues 10
General Procedure M (see Scheme 5)

Compound 9a (5.3 g, 14.62 mmol) was dissolved in pyridine (59 ml) to give a colorless solution. Acetic anhydride (41 ml) was added and the reaction mixture was stirred for 16 h at room temperature. The reaction mixture was poured into 4N hydrochloric acid (250 ml) and extracted with ethyl acetate (3×50 ml). The intermediate was crystallized from ethanol (25 ml, heat to 80° C. and cool slowly with stirring) to give compound 10a as white crystals (4.68 g, 72%). $^1$H NMR (CDCl$_3$): δ 0.66 (d, J=7 Hz, 3H), 1.87 (m, 1H), 2.28 (s, 3H), 2.33 (s, 3H), 2.76 (dd, J1=11 Hz, J2=14 Hz, 1H), 2.94 (dd, J1=3 Hz, J2=14 Hz, 1H), 3.22 (m, 2H), 3.51 (dd, J1=5 Hz, J2=14 Hz, 1H), 3.60 (m, 1H), 6.91-7.31 (m, 11H).

The enantiomers of racemate 10a (4.6 g) were separated on a chiral HPLC column (Chiralpak OD 5μ; 5% isopropanol in heptane) to afford single enantiomers 21a (1.95 g; chemical purity 98%) and 22a (2.04 g; chemical purity 95%). The enantiomeric excess (e.e.) of the separated enantiomers was determined on an analytical chiral HPLC column (Chiralpak OD 5μ, 4% isopropanol/heptane): compound 21a: retention time 11.80 min; e.e. 100%; compound 22a: retention time 22.59 min; e.e. 97.9%.

Compound 21a (1.95 g) was dissolved in tetrahydrofuran (60 ml). Lithium hydroxide monohydrate (1.10 g, 26.2 mmol) dissolved in water (2 ml), was added and the reaction mixture was stirred for 2 h at room temperature under nitrogen. Water (100 ml) was added and the intermediate was extracted with ethyl acetat (3×50 ml). The organic layer was dried with sodium sulfate filtered and concentrated. The crude product was purified by preparative HPLC (reversed phase acetonitrile/water 40-60) and freeze dried to give the compound 11a as white solid (1.22 g, 3.36 mmol, 100% ee). The absolute stereochemistry of compound 11a was determined by Vibrational Circular Dichroism (VCD) spectroscopy to be (6S, 7S, 8S).

Example 15

4-(6-Acetoxy-3-ethyl-4-(2-fluorobenzyl)-1,2-dihydronaphthalen-2-yl)phenyl acetate (compound 24)

Prepared according to General Procedure M, starting from compound 23: 62% yield. $^1$H NMR (CDCl$_3$): δ 1.03 (t, J=9 Hz, 3H), 1.90 (m, 1H), 2.22 (s, 3H), 2.26 (s, 3H), 2.37 (m, 1H), 2.93 (dd, J1=3 Hz, J2=17 Hz, 1H), 3.34 (dd, J1=9 Hz, J2=17 Hz, 1H), 3.66 (dd, J1=3 Hz, J2=9 Hz, 1H), 3.93 (AB, J1=17 Hz, J2=42, 2H), 6.77 (dd, J1=3 Hz, J2=9 Hz, 1H), 6.83 (d, J=3 Hz, 1H), 6.98 (AB, J1=9 Hz, J2=82, 4H).

According to General Procedure M (unless indicated otherwise) the compounds in Table 4 were prepared:

TABLE 4

Compounds prepared as described in General Procedure M.

| Compound (racemate) | Name | Structure | Chiral retention enantiomer 21 | HPLC time | e.e. (%) | Chiral retention enantiomer 22 | HPLC time | e.e. (%) |
|---|---|---|---|---|---|---|---|---|
| 10a | 4-(6-acetoxy-4-(2-fluorobenzyl)-3-methyl-1,2,3,4-tetrahydronaphthalen-2-yl)phenyl acetate | 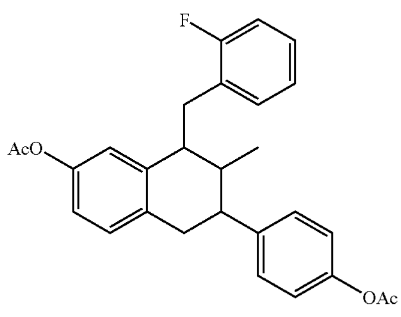 | 21a: | 11.80 (§) | 100 | 22a: | 22.59 (§) | 97.9 |
| 10b (♠) | 4-(6-acetoxy-4-(2-fluorobenzyl)-3-ethyl-1,2,3,4-tetrahydronaphthalen-2-yl)phenyl acetate | 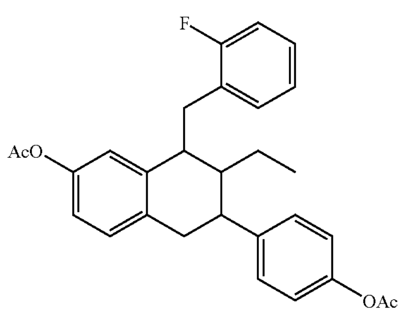 | 21b: | 13.36 (#) | 100 | 22b: | 19.92 (#) | 93.7 |

TABLE 4-continued

Compounds prepared as described in General Procedure M.

| Compound (racemate) | Name | Structure | Chiral retention enantiomer 21 | HPLC time 21 | e.e. (%) | Chiral retention enantiomer 22 | HPLC time 22 | e.e. (%) |
|---|---|---|---|---|---|---|---|---|
| 10i | (4-(6-acetoxy-4-(2,6-difluorobenzyl)-3-methyl-1,2,3,4-tetrahydronaphthalen-2-yl) phenyl acetate | 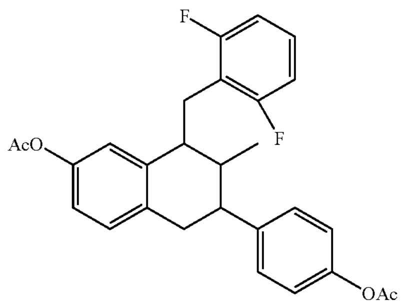 | 21i: | 10.85 (#) | 100 | 22i: | 16.94 (#) | 100 |

Notes:
(§) HPLC retention time on Chiralpak OD 5µ column 4.6 × 250 mm (4% isopropanol/heptane, flow 1 ml/min)
(#) HPLC retention time on Chiralpak OD 5µ column 4.6 × 250 mm (3% ethanol/heptane, flow 1 ml/min)

(♣) Prepared from compound 24 according to General Procedure J, followed by chiral HPLC separation of the enantiomers according to procedure H.

According to General Procedure L or M the following compounds 11 and 12 were prepared:

TABLE 5

Compounds 11 prepared as described in General Procedure L or M.

| Compound | Name | Structure | General Procedure | Purity (%) | Chiral HPLC retention time | e.e. (%) |
|---|---|---|---|---|---|---|
| 11a | (6S,7S,8S)-8-(2-fluorobenzyl)-6-(4-hydroxyphenyl)-7-methyl-5,6,7,8-tetrahydronaphthalen-2-ol | 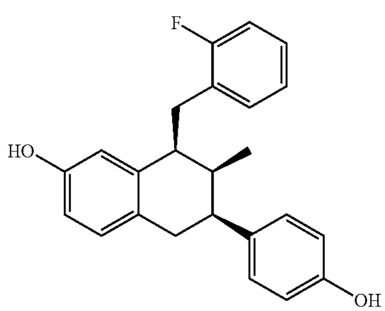 | M | 99.7 (@) | 16.25 (£) | 100 |
| 11b | (6S,7S,8S)-7-ethyl-8-(2-fluorobenzyl)-6-(4-hydroxyphenyl)-5,6,7,8-tetrahydronaphthalen-2-ol | 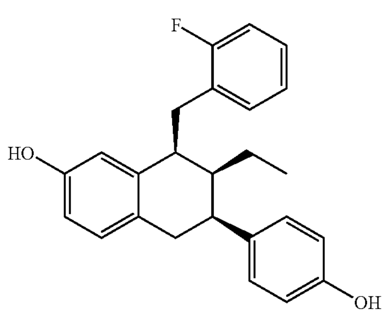 | M | 99.6 ($) | 12.29 (♣) | 97.0 |

TABLE 5-continued

Compounds 11 prepared as described in General Procedure L or M.

| Compound | Name | Structure | General Procedure | Purity (%) | Chiral HPLC retention time | e.e. (%) |
|---|---|---|---|---|---|---|
| 11f | (6S,7S,8S)-8-(3-fluorobenzyl)-6-(4-hydroxyphenyl)-7-methyl-5,6,7,8-tetrahydronaphthalen-2-ol | 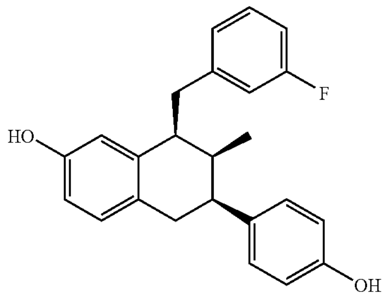 | M | 97.2 | 16.31 (‡) | 95.6 |
| 11g | (6S,7S,8S)-8-(4-fluorobenzyl)-6-(4-hydroxyphenyl)-7-methyl-5,6,7,8-tetrahydronaphthalen-2-ol | 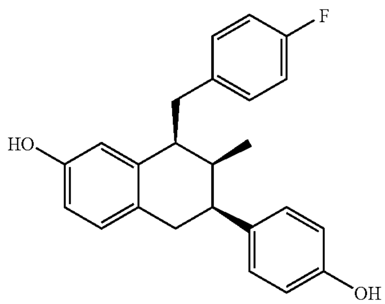 | M | 99.8 | 28.93 (‡) | 98.4 |
| 11i | (6S,7S,8S)-8-(2,6-difluorobenzyl)-6-(4-hydroxyphenyl)-7-methyl-5,6,7,8-tetrahydronaphthalen-2-ol | 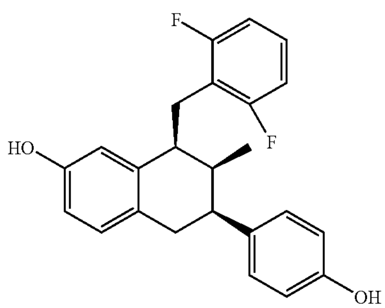 | M | 99.3 (*) | 10.85 (♪) | 100 |
| 11j | 2-(((1S,2S,3S)-7-hydroxy-3-(4-hydroxyphenyl)-2-methyl-1,2,3,4-tetrahydronaphthalen-1-yl)methyl)benzonitrile | 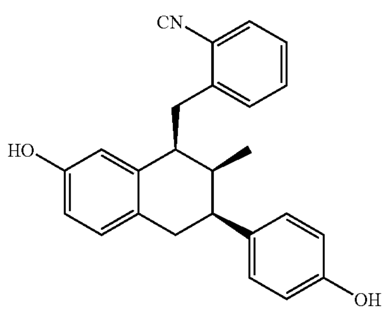 | L | 97.9 (¤) | 19.67 (§) | 100 |
| 11q | (6S,7S,8S)-7-ethyl-6-(3-fluoro-4-hydroxyphenyl)-8-(2-fluorobenzyl)-5,6,7,8-tetrahydronaphthalen-2-ol | 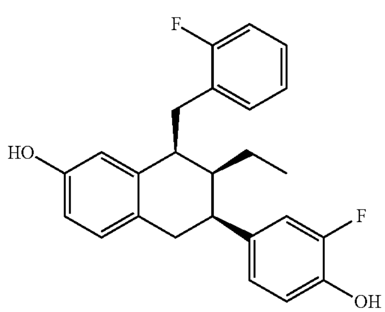 | L | 96.1 | 13.91 (‡) | 97.7 |

TABLE 5-continued

Compounds 11 prepared as described in General Procedure L or M.

| Compound | Name | Structure | General Procedure | Purity (%) | Chiral HPLC retention time | e.e. (%) |
|---|---|---|---|---|---|---|
| 11w | (6S,7S,8S)-7-ethyl-8-(4-fluorobenzyl)-6-(4-hydroxyphenyl)-5,6,7,8-tetrahydronaphthalen-2-ol | 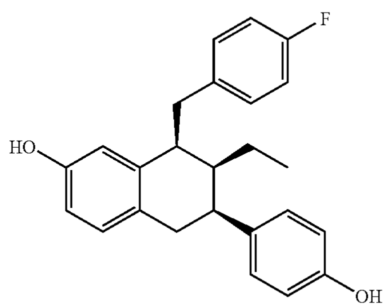 | L | 99.4 (*) | 12.77 (#) | 100 |

Notes:

§) HPLC retention time on Chiralpak AS 5μ column 4.6 × 250 mm (20% isopropanol/heptane, flow 1 ml/min)

£) HPLC retention time on Chiralpak AS 5μ column 4.6 × 250 mm (16% isopropanol/heptane, flow 1 ml/min)

‡) HPLC retention time on Chiralpak AS 5μ column 4.6 × 250 mm (15% isopropanol/heptane, flow 1 ml/min)

♠) HPLC retention time on Chiralpak AS 5μ column 4.6 × 250 mm (12% ethanol/heptane, flow 1 ml/min)

) HPLC retention time on Chiralpak AD 5μ column 4.6 × 250 mm (11% ethanol/heptane, flow 1 ml/min)

♪) HPLC retention time on Chiralpak AD 5μ column 4.6 × 250 mm (9% ethanol/heptane, flow 1 ml/min)

□): purity based on HPLC on 5μ C18 luna column, gradient acetonitrile in water over 12 min gradient 20 to 100%;

*): purity based on HPLC on 5μ C18 luna column, gradient acetonitrile in water over 12 min gradient 30 to 90%

$): purity based on HPLC on 5μ C18 luna column, 5 min isocratic followed by gradient acetonitrile in water over 12 min gradient 20 to 100%

@) purity based on HPLC on 5μ C18 luna column, gradient acetonitrile in water over 12 min gradient 10 to 90%

TABLE 6

Compounds 12 prepared as described in General Procedure L or M.

| Compound | Name | Structure | General Procedure | Purity (%) | Chiral HPLC retention time | e.e. (%) |
|---|---|---|---|---|---|---|
| 12a | (6R,7R,8R)-8-(2-fluorobenzyl)-6-(4-hydroxyphenyl)-7-methyl-5,6,7,8-tetrahydronaphthalen-2-ol | 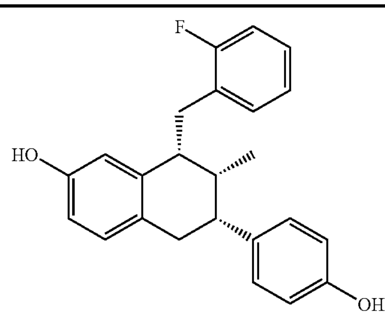 | M | 99.8 (@) | 12.2 (£) | 100 |
| 12b | (6R,7R,8R)-7-ethyl-8-(2-fluorobenzyl)-6-(4-hydroxyphenyl)-5,6,7,8-tetrahydronaphthalen-2-ol | 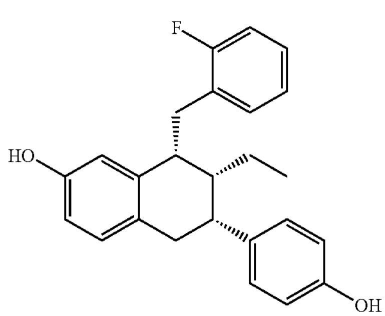 | M | 99.6 (*) | 10.38 (♠) | 100 |

TABLE 6-continued

Compounds 12 prepared as described in General Procedure L or M.

| Compound | Name | Structure | General Procedure | Purity (%) | Chiral HPLC retention time | e.e. (%) |
|---|---|---|---|---|---|---|
| 12f | (6R,7R,8R)-8-(3-fluorobenzyl)-6-(4-hydroxyphenyl)-7-methyl-5,6,7,8-tetrahydronaphthalen-2-ol | 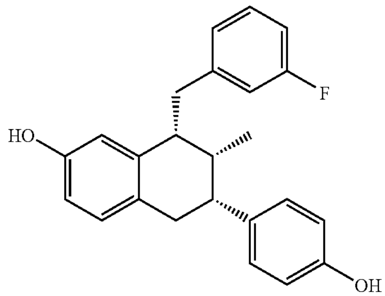 | M | 99.9 | 28.15 (‡) | 99.2 |
| 12g | (6R,7R,8R)-8-(4-fluorobenzyl)-6-(4-hydroxyphenyl)-7-methyl-5,6,7,8-tetrahydronaphthalen-2-ol | 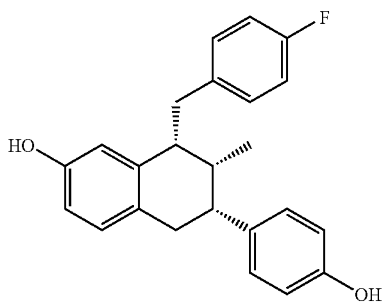 | M | 98.4 | 46.99 (‡) | 88.8 |
| 12i | (6R,7R,8R)-8-(2,6-difluorobenzyl)-6-(4-hydroxyphenyl)-7-methyl-5,6,7,8-tetrahydronaphthalen-2-ol | 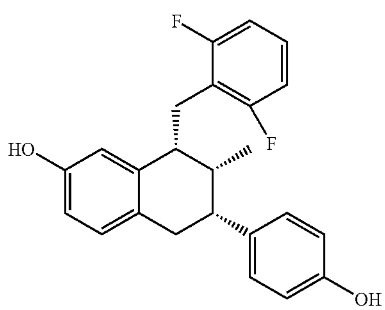 | M | 98.3 ($) | 9.43 (♪) | 100 |
| 12j | 2-(((1R,2R,3R)-7-hydroxy-3-(4-hydroxyphenyl)-2-methyl-1,2,3,4-tetrahydronaphthalen-1-yl)methyl)benzonitrile | 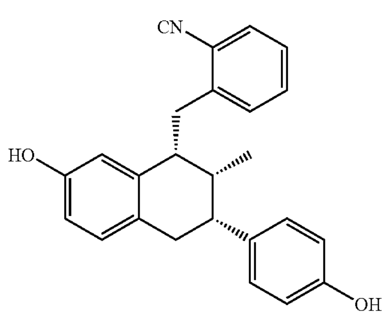 | L | 95.1 (¤) | 33.67 (§) | 98.9 |

TABLE 6-continued

Compounds 12 prepared as described in General Procedure L or M.

| Compound | Name | Structure | General Procedure | Purity (%) | Chiral HPLC retention time | e.e. (%) |
|---|---|---|---|---|---|---|
| 12q | (6R,7R,8R)-7-ethyl-6-(3-fluoro-4-hydroxyphenyl)-8-(2-fluorobenzyl)-5,6,7,8-tetrahydronaphthalen-2-ol | 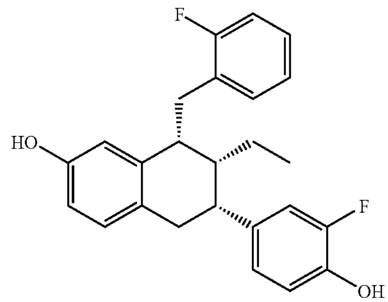 | L | 95.7 | 94.91 (‡) | 97.6 |
| 12w | (6R,7R,8R)-7-ethyl-8-(4-fluorobenzyl)-6-(4-hydroxyphenyl)-5,6,7,8-tetrahydronaphthalen-2-ol | 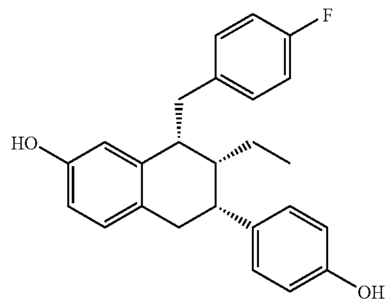 | L | 93.9 ($) | 15.84 (#) | 100 |

Notes:
§) HPLC retention time on Chiralpak AS 5µ column 4.6 × 250 mm (20% isopropanol/heptane, flow 1 ml/min)
£) HPLC retention time on Chiralpak AS 5µ column 4.6 × 250 mm (16% isopropanol/heptane, flow 1 ml/min)
‡) HPLC retention time on Chiralpak AS 5µ column 4.6 × 250 mm (15% isopropanol/heptane, flow 1 ml/min)
♠) HPLC retention time on Chiralpak AS 5µ column 4.6 × 250 mm (12% ethanol/heptane, flow 1 ml/min)
) HPLC retention time on Chiralpak AD 5µ column 4.6 × 250 mm (11% ethanol/heptane, flow 1 ml/min)
♪) HPLC retention time on Chiralpak AD 5µ column 4.6 × 250 mm (9% ethanol/heptane, flow 1 ml/min)
@) purity based on HPLC on 5µ C18 luna column, gradient acetonitrile in water over 12 min gradient 10 to 90%
◻): purity based on HPLC on 5µ C18 luna column, gradient acetonitrile in water over 12 min gradient 20 to 100%
$): purity based on HPLC on 5µ C18 luna column, gradient acetonitrile in water over 12 min gradient 30 to 90%
*): purity based on HPLC on 5µ C18 luna column, 5 min isocratic followed by gradient acetonitrile in water over 12 min gradient 20 to 100%

Example 16

The compounds 9, 10, 11 and 12 were tested for their estrogen receptor affinity, both as an agonist and as an antagonist.

Determination of competitive binding to cytoplasmic human estrogen receptor α or β from recombinant CHO cells was used to estimate the (relative) affinity of a test compound for estrogen receptors present in the cytosol of recombinant Chinese hamster ovary (CHO) cells, stably transfected with the human estrogen receptor a (hERα) or β receptor (hERβ), as compared with estradiol (E2).

The estrogenic and antiestrogenic activity of compounds was determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity of a test compound to stimulate the transactivation of the enzyme luciferase mediated via the estrogen receptors hERα or hERβ is expressed in nM. The assay was performed as described by De Gooyer et al., *Steroids* 68 (2003), 21-30.

TABLE 7

ERβ and ERα transactivation data

| Compound | ERβ agonistic EC50 (nM) | ERβ/ERα ratio | ERβ eudismic ratio | ERα eudismic ratio |
|---|---|---|---|---|
| 8n | 2.5 | >40 | | |
| 9a | 0.45 | 193 | | |
| 9b | 0.35 | 77 | | |
| 9c | 0.40 | 33 | | |
| 9d | 0.68 | 51 | | |
| 9e | 0.42 | 18 | | |
| 9f | 3.0 | >33 | | |
| 9g | 2.3 | >43 | | |
| 9h | 0.60 | >167 | | |
| 9i | 0.98 | >102 | | |
| 9j | 0.56 | 605 | | |
| 9k | 0.49 | >204 | | |
| 9l | 0.33 | 339 | | |
| 9m | 31 | 2 | | |
| 9o | 0.17 | 42 | | |
| 9p | 0.30 | >333 | | |
| 9q | 1.5 | >67 | | |
| 9r | 1.2 | >83 | | |
| 9s | 4.7 | >21 | | |
| 9v | 1.6 | >63 | | |
| 9w | 0.91 | 12 | | |
| 9y | 12 | >8 | | |

TABLE 7-continued

ERβ and ERα transactivation data

| Compound | ERβ agonistic EC50 (nM) | ERβ/ERα ratio | ERβ eudismic ratio | ERα eudismic ratio |
|---|---|---|---|---|
| 10i | 1.3 | >77 | | |
| 11a | 0.38 | 189 | >263 | >1.4 |
| 11b | 0.15 | 167 | 93 | 0.9 |
| 11f | 1.2 | 21 | 13 | >4 |
| 11g | 1.4 | 19 | 9 | >4 |
| 11i | 0.47 | >213 | >212 | NM |
| 11j | 0.14 | >714 | 143 | NM |
| 11q | 0.59 | >169 | 7 | <0.3 |
| 11w | 0.36 | 61 | 42 | 0.4 |
| 11x | 1.3 | 19 | >77 | >4 |

NM = not meaningful

Example 17

Selected compounds were tested in a short-term prostate apoptosis and proliferation model in castrated rats.

Intact mature male Wistar rats (350-400 g) were castrated and left to recover for 1 week. 7 days after the castration rats received a single subcutaneous injection of testosterone buciclate (TB), a long-acting testosterone ester, in arachis oil (20 mg/kg) with a volume of 1 ml/kg and were subsequently treated once daily orally for 3 days with the test substance at doses between 0 and 1000 μg/kg, dissolved in gelatin/mannitol and dosed with a volume of 1 ml/kg.

At the end of the experiment rats were euthanized, the prostates were removed, weighed and processed for histology.

Apoptosis of the acinar epithelium of the ventral prostate was determined with TUNEL (Terminal unscheduled nick end labeling) staining. Apoptotic cells show nuclear DNA fragmentation and the TUNEL assay end-labels the fragmented DNA by incorporating biotinylated dUTP at the 3'-OH DNA ends using the enzyme Terminal deoxynucleotidyl Transferase (TdT). Positively stained cells are counted per acinus (glandular unit) in the ventral prostate. Proliferation of the acinar epithelium of the ventral prostate was determined by immunohistochemical staining with an antibody directed against Ki67 (clone Mib5). Positively stained cells are counted per acinus (glandular unit) in the ventral prostate. Statistical significance is determined as compared to TB alone by one-way ANOVA.

For compound 11a a statistically significant (p<0.01) increase in epithelial cell apoptosis was observed in this assay, with a minimal active dose (MAD) of 3 μg/kg. At this dose a decrease in epithelial cell proliferation was observed as compared to TB-alone treated rats.

Example 18

A number of compounds 9, 11 and 12 were tested on metabolic stability in human hepatocytes. The hepatic stability was compared to corresponding chroman compounds 25, 26 or 27 (see structures below).

Test compounds were diluted to 3 μM in incubation medium. Then 40 μl of the 3 μM test compounds was pipetted into a 96 well microtiter plate (flat bottom). Hepatocytes (stored at −140° C.) were thawed in a 37° C. water bath. The cells were resuspended into pre-warmed thawing medium and were centrifuged for 5 minutes at 50 g at room temperature. The supernatant was discarded and the remaining cell pellet was resuspended in warm incubation medium and diluted to 7.5 E5 cells/ml. Then 80 μl of the cell suspension was added to each well of the 96 well microtiter plate containing the test compounds. The resulting mixture was incubated at 37° C. and was sampled at t=0, 5, 30, 60, and 120 min. The samples were analyzed by LC-MS/MS to determine the content of unchanged test compound. Based on the rate of reduction of the content of test compound over time, the half-live (T½) was calculated. The hepatic stability is summarized in Table 8.

TABLE 8

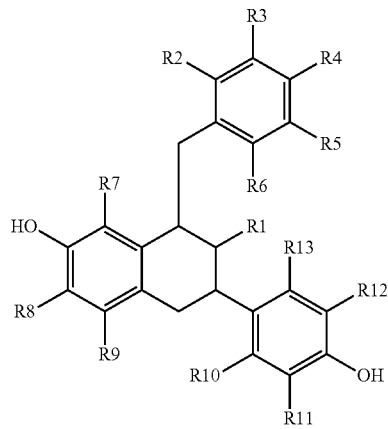

9 (racemate)
11 (eutomer)
12 (distomer)

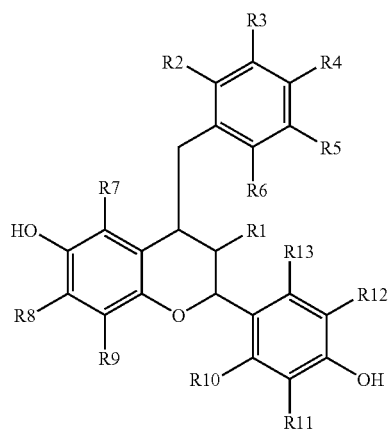

25 (racemate)
26 (eutomer)
27 (distomer)

Metabolic stability in human hepatocytes

| Tetrahydro-naphthalen-2-ol | Human hepatocyte T ½ (min) | Chroman (‡) | Human hepatocyte T ½ (min) |
|---|---|---|---|
| 9b | 70.0 | 25b | 44.8 |
| 9j | 37.4 | 25j | 40.4 |
| 9o | 73.2 | 25o | 71.5 |
| 9p | >120 | 25p | 48.5 |
| 9r | 57.9 | 25r | 24.0 |
| 9s | 96.5 | 25s | 56.9 |
| 9v | 69.8 | 25v | 53.6 |
| 9y | 109.6 | 25v | 58.7 |
| 11a | 40.5 | 26a | 35.3 |
| 11b | 40.7 | 26b | 35.6 |
| 11i | 29.4 | 26i | 26.2 |
| 11q | 82.2 | 26q | 45.5 |
| 12a | 66.9 | 27a | 33.4 |
| 12i | 67.1 | 27i | 45.2 |
| 12j | 33.7 | 27j | 24.1 |
| 12q | >120 | 27q | 47.4 |

Note:
(‡) the one-letter extension in the codes of chromans 25, 26 and 27 indicates the substitution pattern of the compounds. The substitution pattern R1-R13 of a compound 25, 26 or 27 is identical to the substitution pattern of the corresponding tetrahydronaphthalen-2-ol 9, 11 or 12 with the same one-letter extension.

The invention claimed is:
1. A tetrahydronaphthalen-2-ol derivative according to Formula 1

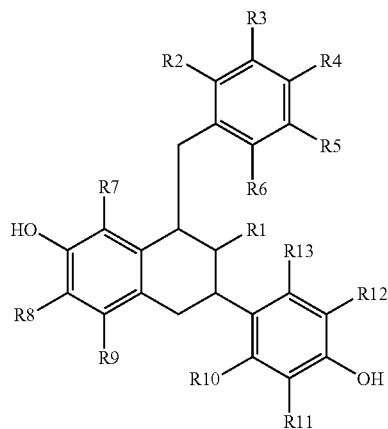

Formula 1 wherein
R1 is (C1-C4)alkyl, (C2-C4)alkenyl or (C2-C4)alkynyl, independently optionally substituted with one or more halogen, R1 having a cis-orientation in relation to both the exocyclic phenyl group at the 6-position and the benzyl group at the 8-position of the skeleton;
R2-R13 are independently H, halogen, CN, OH, (C1-C4) alkyl, optionally substituted with one or more halogen, or (C1-C2)alkyloxy;
or a prodrug or an isotopically-labelled derivative thereof.

2. A tetrahydronaphthalen-2-ol derivative according to claim 1, wherein R1 is (C1-C4)alkyl, optionally substituted with one or more halogen.

3. A tetrahydronaphthalen-2-ol derivative of Formula 1 according to claim 1

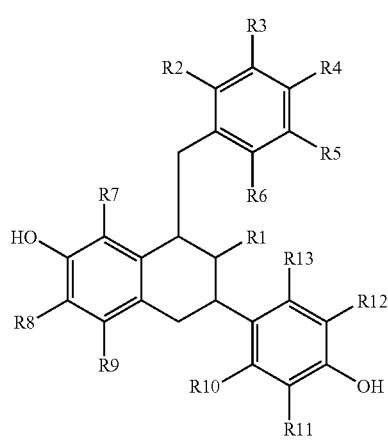

Formula 1 wherein
R1 is (C1-C4)alkyl, (C2-C4)alkenyl or (C2-C4)alkynyl, independently optionally substituted with one or more halogen, R1 having a cis-orientation in relation to both the exocyclic phenyl group at the 6-position and the benzyl group at the 8-position of the skeleton;
R2-R6 are independently H, halogen, CN, OH, (C1-C4) alkyl, optionally substituted with one or more halogen or (C1-C2)alkoxy, with a maximum of two OH groups;

R7-R13 are independently H, halogen, CN, (C1-C4)alkyl, optionally substituted with one or more halogen or (C1-C2)alkoxy;
or a prodrug thereof.

4. A tetrahydronaphthalen-2-ol derivative of Formula 1 according to claim 1

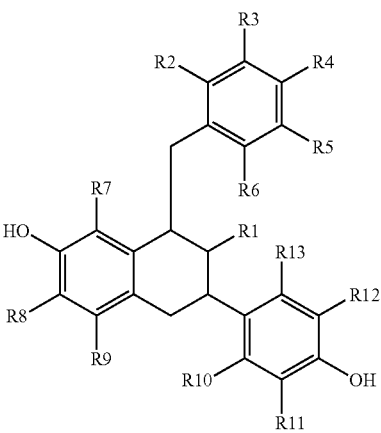

Formula 1 wherein
R1 is (C1-C4)alkyl, (C2-C4)alkenyl or (C2-C4)alkynyl, independently optionally substituted with one or more halogen, R1 having a cis-orientation in relation to both the exocyclic phenyl group at the 6-position and the benzyl group at the 8-position of the skeleton;
R2-R13 are independently H, halogen, CN, OH, (C1-C4) alkyl, optionally substituted with one or more halogen or (C1-C2)alkoxy, with a maximum of five R2-R13 groups unequal to H.

5. A tetrahydronaphthalen-2-ol derivative of Formula 1 according to claim 1

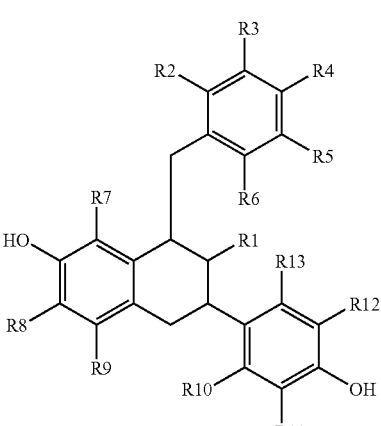

Formula 1 wherein
R1 is methyl, ethyl or propyl;
R2 is H, chlorine, fluorine, CN, methoxy or methyl;
R3-R7 and R10 are H or fluorine;
R8, R9, R11 and R13 are H;
R12 is H, fluorine or methyl.

6. A tetrahydronaphthalen-2-ol derivative of Formula 2 according to claim 1

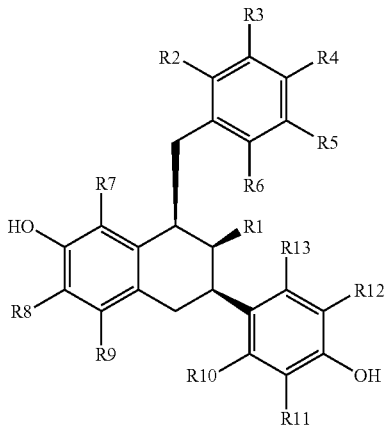

Formula 2 wherein
R1 is methyl, ethyl or propyl;
R2 is H, chlorine, fluorine, CN, methoxy or methyl;
R3-R7 and R10 are H or fluorine;
R8, R9, R11 and R13 are H;
R12 is H, fluorine or methyl.

7. A tetrahydronaphthalen-2-ol derivative according to claim 6 selected from the group consisting of compounds according to Formula 2 wherein R1 is methyl, R2 is fluorine, and R3-R13 are H; R1 is ethyl, R2 is fluorine, and R3-R13 are H; R1 is methyl, R2 and R6 are fluorine, and R3-R5 and R7-R13 are H; R1 is methyl, R2 is CN, and R3-R13 are H; R1 is ethyl, R2 and R12 are fluorine, and R3-R11 and R13 are H; and R1 is ethyl, R4 is fluorine, and R2-R3 and R5-R13 are H.

8. A tetrahydronaphthalen-2-ol derivative according to claim 7, wherein R1 is methyl, R2 is fluorine, and R3-R13 are H.

9. A pharmaceutical composition comprising a tetrahydronaphthalen-2-ol derivative according to claim 1 and one or more pharmaceutically acceptable excipients.

10. A method for the treatment of a mammal suffering from a disease or disorder selected from the group consisting of lower urinary tract symptoms, benign prostate hyperplasia, and prostate cancer, the method comprising administering a therapeutically effective amount of a tetrahydronaphthalen-2-ol derivative according to claim 1.

* * * * *